United States Patent
Fiege et al.

(10) Patent No.: US 9,507,886 B2
(45) Date of Patent: Nov. 29, 2016

(54) MULTI-OBJECTIVE RADIATION THERAPY OPTIMIZATION METHOD

(76) Inventors: Jason Fiege, Winnipeg (CA); Boyd McCurdy, Winnipeg (CA); Peter Potrebko, Mullica Hill, NJ (US); Andrew Cull, The Pas (CA); Heather Champion, Winnipeg (CA); Murphy Berzish, Waterloo (CA)

( * ) Notice: Subject to any disclaimer, the term of this patent is extended or adjusted under 35 U.S.C. 154(b) by 916 days.

(21) Appl. No.: 13/639,400
(22) PCT Filed: Jun. 7, 2011
(86) PCT No.: PCT/CA2011/050347
§ 371 (c)(1),
(2), (4) Date: Apr. 19, 2013
(87) PCT Pub. No.: WO2011/153639
PCT Pub. Date: Dec. 15, 2011

(65) Prior Publication Data
US 2013/0197878 A1 Aug. 1, 2013

Related U.S. Application Data

(60) Provisional application No. 61/352,091, filed on Jun. 7, 2010.

(51) Int. Cl.
*G06F 7/60* (2006.01)
*G06F 17/10* (2006.01)
(Continued)

(52) U.S. Cl.
CPC ......... *G06F 17/5009* (2013.01); *A61N 5/1031* (2013.01); *G06F 19/325* (2013.01); *G06F 19/3481* (2013.01); *G06N 3/126* (2013.01); *A61N 2005/1032* (2013.01)

(58) Field of Classification Search
CPC ........... G06F 17/5009; G06F 19/3481; G06F 19/325; G06N 3/126; A61N 5/1031; A61N 2005/1032
USPC ................................................. 378/65; 703/2
See application file for complete search history.

(56) References Cited

U.S. PATENT DOCUMENTS

| 7,391,026 B2 | 6/2008 | Trinkaus et al. |
| 2005/0038762 A1 | 2/2005 | Grefenstette |

(Continued)

FOREIGN PATENT DOCUMENTS

WO 2005072825 8/2005

OTHER PUBLICATIONS

Thieke, Christian et al., "A New Concept for Interactive Radiotherapy Planning with Multicriteria Optimization: First Clinical Evaluation", 2007, Radiotherapy and Oncology 85, 2007, Elsevier Ireland Ltd.*

(Continued)

*Primary Examiner* — Cedric D Johnson
(74) *Attorney, Agent, or Firm* — Ryan W. Dupuis; Kyle R. Satterthwaite; Ade & Company Inc.

(57) ABSTRACT

A novel and powerful fluence and beam orientation optimization package for radiotherapy optimization, called PARETO (Pareto-Aware Radiotherapy Evolutionary Treatment Optimization), makes use of a multi-objective genetic algorithm capable of optimizing several objective functions simultaneously and mapping the structure of their trade-off surface efficiently and in detail. PARETO generates a database of Pareto non-dominated solutions and allows the graphical exploration of trade-offs between multiple planning objectives during IMRT treatment planning PARETO offers automated and truly multi-objective treatment plan optimization, which does not require any objective weights to be chosen, and therefore finds a large sample of optimized solutions defining a trade-off surface, which represents the range of compromises that are possible.

15 Claims, 15 Drawing Sheets

(51) Int. Cl.
    *G06F 17/50*    (2006.01)
    *A61N 5/10*     (2006.01)
    *G06F 19/00*    (2011.01)
    *G06N 3/12*     (2006.01)

(56) References Cited

U.S. PATENT DOCUMENTS

2005/0207531 A1* 9/2005 Dempsey ............. A61N 5/1031
                                                    378/65
2009/0037150 A1* 2/2009 Craft .................. G06F 19/3437
                                                     703/1

OTHER PUBLICATIONS

Haas, Olivier Cyrille Louis, "Radiotherapy Treatment Planning: Chapter 5—Hybrid Genetic Algorithms Applied to Radiotherapy Treatment Planning", 1999, Springer.*
Zhu, Lei et al., "Search for IMRT Inverse Plans with Piecewise Constant Fluence Maps using Compressed Sensing Techniques", May 2009, Med. Phys. 36, Am. Assoc. Phys. Med.*
Stein, Jorg et al., "Number and Orientations of Beams in Intensity-Modulated Radiation Treatments", 1997, med. Phys. 24, Am. Assoc. Phys. Med.*
Cotrutz, C. et al., "A Multiobjective Gradient-Based Dose Optimization Algorithm for External Beam Conformal Radiotherapy", Jul. 19, 2001, Physics in Medicine and Biology 46, Institute of Physics Publishing.*
Handl, Julia et al., "Multiobjective Optimization in Bioinformatics and Computational Biology", Apr.-Jun. 2007, IEEE/ACM Transactions on Computational Biology and Bioinformatics, vol. 4, No. 2, IEEE.*
Bedford JL et al., "Direct-Aperture Optimization Applied to Selection of Beam Orientations in Intensity-Modulated Radiation Therapy", Dec. 29, 2006, Physics in Medicine and Biology 52, Institute of Physics Publishing.*
Wang, Xiaochun et al., Development of Methods for Beam Angle Optimization for IMRT Using an Accelerated Exhaustive Search Strategy, 2004, Int. J. Radiation Oncology Biol. Phys., vol. 60, No. 4, Elsevier Inc.*
Anders Anhesjo, Collapsed cone convolution of radiant energy for photon dose calculation in heterogeneous media, Am. Assoc. Phys. Med., Med. Phys. 16(4), Jul./Aug. 1989, p. 577.
Jean-Francois Aubry, Multiobjective optimization with a modified simulated annealing algorithm for external beam radiotherapy treatment planning, Am. Assoc. Phys. Med., Med. Phys. 33 (12), Dec. 2006, p. 4718.
Sebastiaan Breedveld, Pascal R.M. Storchi, Marleen Keijzer, Arnold W. Heemink and Ben J.M. Heijmen, A novel approach to multi-criteria inverse planning for IMRT, Phys. Med. Biol. 52 (2007) pp. 6339-6353, Physics in Medicine and Biology, 2009 IOP Publishing Ltd.
K. Chytyk, B.M.C. McCury, Comprehensive fluence model for absolute portal does image prediction, Am. Assoc. Phys. Med., Med. Phys. 36 (4), Apr. 2009, p. 1389.
C. Cotrutz, M. Lahanas, C. Kappas and D. Baltas, A multiobjective gradient-based dose optimization algorithm for external beam conformal radiotherapy, Physics in Medicine and Biology, IOP Publishing Ltd., Phys. Med. Biol. 46 (2001) pp. 2161-2175.
David Craft, Ph.D., Tarek Halabi, Ph.D., Helen A. Shih, M.D., and Thomas Bortfeld, Ph.D., An Approach for Practical Multiobjective IMRT Treatment Planning, Int. J. Radiation Oncology Biol. Phys. vol. 69, No. 5, pp. 1600-1607, 2007.
David Craft and Michael Monz, Simultaneous navigation of multiple Pareto surfaces, with an application to multicriteria IMRT planning with multiple beam angle configurations, Am. Assoc. Phys. Med., Med. Phys. 37(2), Feb. 2010, p. 736.
David Craft, Tarek Halabi and Thomas Bortfeld, Exploration of tradeoffs in intensity-modulated radiotherapy, Physics in Medicine and Biology, Phys. Med. Biol. 50 (2005) pp. 5857-5868.
David Craft and Thomas Bortfeld, How many plans are needed in an IMRT multi-objective plan database?, Physics in Medicine and Biology, Phys. Med. Biol. 53 (2008) pp. 2785-2796.
Shiva K. Das, A Method to dynamically balance intensity modulated radiotherapy does between organs-at-risk, Am. Assoc. Phys. Med., Med. Phys. 36 (5), May 2009, p. 1744.
J.O. Deasy, Multiple local minima in radiotherapy optimization problems with dose-volume constraints, Am. Assoc. Phys. Med., Med. Phys. 24 (7), Jul. 1997, p. 1157.
Jason D. Fiege, Doug Johnstone, Russel O. Redman, and Paul A. Feldman, A Genetic Algorithm-Based Exploration of Three Filament Models: A Case for the Magnetic Support of the G11.11-0.12 Infrared-Dark Cloud, The Astrophysical Journal, 616:925-942, Dec. 1, 2004, p. 925.
John D. Fenwick and Juan Pardo-Montero, Homogenized blocked arcs for multicriteria optimization of radiotherapy: Analytical and numerical solutions, Am. Assoc. Phys. Med., Med. Phys. 37 (5), May 2010, p. 2194.
Jason D. Fiege, Computational Intelligence Techniques for Submillimetre Polarization Modeling, Astronomical Polarimetry: Current Status and Future Directions, ASP Conference Series, vol. 343, 2005, p. 171.
Carlos M. Fonesca and Peter J. Fleming, Genetic Algorithms for Multiobjective Optimization: Formulation, Discussion and Generalization, Dept. Automatic Control and Systems Eng., University of Sheffield, Sheffield S1 4DU, U.K.
Terak Halabi, David Craft and Thomas Forfeld, Dose-volume objectives in multi-criteria optimization, Institute of Physics Publishing, Physics in Medicine and Biology, 51 (2006) pp. 3809-3818.
Aswin L. Hoffman, Alex Y. D. Siem, Dick Den Hertog, Johannes H. A. M. Kaanders and Henk Huizenga, Institute of Physics Publishing, Physics in Medicine and Biology, 51 (2006) pp. 6349-6369.
Theodore S. Hong, M.D., David L. Craft, Ph.D., Fredrik Carlsson, Ph.D. and Thomas R. Bortfeld, Ph.D., Multicriteria Optimization in Intensity-Modulated Radiation Therapy Treatment Planning for Locally Advanced Cancer of the Pancreatic Head, Int. J. Radiation Oncology Biol. Phys. vol. 72, No. 4, pp. 1208-1214, 2008.
Qing Hou, Jun Wang, Yan Chen and James M. Galvin, Beam orientation optimization for IMRT by a hybrid method of the genetic algorithm and the simulated dynamics, Am. Assoc. Phys. Med., Med. Phys. 30 (9) Sep. 2003, p. 2360.
Tommy Knoos, Ph.D., Ingrid Kristensen, R.N. and Per Nilsson, Ph.D., Volumertric and Dosimetric Evaluation of Radiation Treatment Plans: Radiation Conformity Index, Int. J. Radiation Oncology Biol. Phys. vol. 42, No. 5, pp. 1169-1176, 1998.
Yongjie Li, Jonathan Yao and Dezhong Yao, Automatic beam angle selection in IMRT planning using genetic algorithm, Institute of Physics Publishing, Physics in Medicine and Biology, 49 (2004) pp. 1915-1932.
M. Monz, K. H. Kufer, T. R. Bortfeld and C. Thieke, Pareto navigation-algorithmic foundation of interactive multi-criteria IMRT planning, IOP Publishing, Physics in Medicine and Biology, 53 (2008) pp. 985-998.
Andrzej Niemierko, Reporting and analyzing dose distributions: A concept of equivalent uniform dose, Am. Assoc. Phys. Med., Med. Phys. 24 (1) Jan. 1997, p. 103.
Juan Pardo-Montero and John D. Fenwick, An approach to multiobjective optimization of rotational therapy, Am. Assoc. Phys. Med., Med. Phys. 36 (7) Jul. 2009, p. 3292.
Peter S. Potrebko, Boyd M. C. McCurdy, James B. Butler, Adel S. El-Gubtan, Zoann Nugent, A simple geometric algorithm to predict optimal starting gantry angles using equiangular-spaced beams for intensity modulated radiation therapy of prostate cancer, Am. Assoc. Phys. Med., Med. Phys. 34 (10) Oct. 2007, p. 3951.
A. B. Pugachev, A. L. Boyer and L. Xing, Beam orientation optimization in intensity-modulated radiation treatment planning, Am. Assoc. Phys. Med., Med. Phys. 27 (6) Jun. 2000, p. 1238.
Nicol N. Shraudolph, A Fast, Compact, Approximation of the Exponential Function, Neural Computation, 11, 1999, Massachusetts Institute of Technology, pp. 853-862.
Eduard Schriebmann and Lei Xing, Feasibility study of beam orientation class-solutions for prostate IMRT, Am. Assoc. Phys. Med., Med. Phys. 31 (10) Oct. 2004, p. 2863.

(56) References Cited

OTHER PUBLICATIONS

Tobias Spalke, David Craft and Thomas Bortfeld, Analyzing the main trade-offs in multiobjective radiation therapy treatment planning databases, IOP Publishing, Physics in Medicine and Biology, 54 (2009) pp. 3741-3754.

Jorg Stein, Radhe Mohan, Xiao-Hong Wang, Thomas Bortfeld, Qiuwen Wu, Konrad Presier, C. Clifton Ling, and Wolfgang Shlegel, Number and orientations of beams in intensity-modulated radiation treatments, Am. Assoc. Phys. Med., Med. Phys. 24 (2) Feb. 1997, p. 149.

Christian Thieke, Karl-Heinz Kufer, Michael Monz, Alexander Scherrer, Fernando Alonso, Uwe Oelfke, Peter E. Huber, Jurgen Debus, Thomas Bortfeld, A new concept for interactive radiotherapy planning with mulicriteria optimization: First clinical evaluation, Radiotherapy and Oncology 85 (2007) pp. 292-298, www.thegreenjournal.com.

Haas, O.C.L., Burnham, K. J. and Mills, J. A., "Hybrid Optimisation Technique for Radiotherapy Treatment Planning", Control Theory and Applications Centre, Conventry University, Coventry UK, 3, Sep. 1998, pp. 368-372.

Zhu Lei and Zing Lei, "Search for IMRT Inverse Plans with Piecewise Constant Fluence Maps Using Compressed Sensing Techniques", Medical Physics, vol. 36, No. 5, Apr. 27, 2009, pp. 1895-1905.

* cited by examiner

MULTI-OBJECTIVE RADIATION THERAPY OPTIMIZATION METHOD

FIELD OF THE INVENTION

The present invention relates to an optimization method for a multi-objective optimization problem comprising a planning target volume (PTV) surrounded by organs-at-risk (OARs) in a patient to be treated using radiation.

BACKGROUND

The objectives of planning treatment using intensity modulated radiation therapy (IMRT) are to deliver a uniform and highly conformal prescribed dose of radiation to a PTV, while also minimizing the dose to each nearby OAR. These objectives are invariably in conflict, such that compromises are necessary.

Intensity-modulated radiation therapy (IMRT) treatment planning requires trade-offs to be made between delivering a prescribed treatment dose to the tumour and sparing the surrounding healthy tissues. An IMRT radiotherapy treatment plan specifies a gantry and couch angle for each of several beams, as well as a larger group of parameters that encode the fluence pattern for each beam orientation. Beam angle selection is known to be a non-convex optimization problem, which is fundamentally more difficult than the convex problem of fluence optimization (Hou, Q., J. Wang, et al., 2003, Med. Phys. 30(9): 2360-7). One of the difficulties in treatment plan optimization is that feasible solutions may heavily depend on the optimization parameters such as beam orientations or weights applied to multiple objectives.

Commercial planning software such as Eclipse (Varian Medical Systems, Palo Alto, Calif.) and Pinnacle (Philips Radiation Oncology Solutions, Andover, Mass.) focus mainly on the fluence optimization part of the problem, and do not solve the full multi-objective problem, leaving clinical users to optimize beam orientations by hand. Thus, clinical treatment planning requires human operators ('treatment planners' or 'dosimetrists') to manually optimize beam orientations, objectives, and/or weights in a time-consuming, trial-and-error process to find some acceptable compromise. This process does not necessarily converge to solutions that are truly optimal, because manual iteration cannot fully explore the enormous parameter space of beam angle combinations and PTV versus OAR dose trade-offs that are possible. Moreover, such an approach samples a highly restricted part of the solution space corresponding to the weights used; many trade-off solutions are never considered unless all possible combinations of weights are explored, which is not feasible in a manual approach. Planning for stereotactic body radiation therapy (SBRT) has many similarities to IMRT treatment planning with notable differences including higher target doses, possibly multiple targets, and often (but not always) more OARs. The present invention improves greatly on the traditional planning process for IMRT and SBRT.

Simultaneous optimization of multiple objectives, using beam orientation and fluence as the optimization parameters requires an optimizer that can escape from local minima in the enormous search space. The genetic algorithm (GA) is an ideal candidate for such a large-scale optimization problem. Beam orientation optimization algorithms incorporating GAs have been presented in the literature (Li et al., Phys. Med. Biol. 49:1915-1932, 2004 and Schreibmann et al., Phys. Med. Biol., 49:747-770, 2004).

Recently, the concept of multi-objective Pareto optimization for IMRT treatment planning has been an active area of research. The concept of Pareto optimality is a mathematical notion that is applied to solve multi-objective problems, where the goal is to optimize more than one fitness function simultaneously and to explore the set of solutions representing trade-offs or compromises between objectives. A Pareto non-dominated solution is defined by the property that no other solution is known that is equivalent or superior in all objectives, and also strictly superior in at least one objective. The Pareto front (or Pareto surface) is the set of all possible Pareto non-dominated solutions, such that it is not mathematically possible to improve performance on any objective function without degrading performance on at least one other objective function. A good multi-objective numerical optimizer is one that efficiently finds a database of non-dominated solutions that approximate and map the structure of the Pareto surface. Multi-objective genetic algorithms are an important class of multi-objective optimizers that can be applied readily to this problem.

Given one or more objective functions for each region-of-interest (ROI), a Pareto non-dominated treatment plan is one for which no other plan is known that is strictly better in at least one objective function while being no worse in every other ROI objective. Currently, commercial treatment planning systems (TPS) are not designed for Pareto optimization. Among treatment planning systems, the present invention is uniquely capable of optimizing several objective functions simultaneously, mapping the detailed structure of their trade-off surface without human interaction during the optimization process, and displaying this information to a human user in an intuitive graphical interface for rapid navigation of a database of optimal solutions to determine the best plan used to treat a patient.

SUMMARY OF THE INVENTION

The invention is comprised of a novel and powerful fluence and beam orientation optimization package for radiotherapy optimization, called PARETO (Pareto-Aware Radiotherapy Evolutionary Treatment Optimization), which makes use of a an existing multi-objective genetic algorithm (Ferret Genetic Algorithm; nQube Technical Computing Corporation, Winnipeg, MB; www.nqube.ca) capable of optimizing several objective functions simultaneously and mapping the structure of their trade-off surface efficiently and in detail. PARETO generates a database of Pareto non-dominated solutions and allows the graphical exploration of trade-offs between multiple planning objectives during IMRT treatment planning. PARETO offers automated and truly multi-objective treatment plan optimization, which does not require any objective weights to be chosen, and therefore finds a large sample of optimized solutions defining a trade-off surface, which represents the range of compromises that are possible.

This patent uses "PARETO", written in all uppercase letters, when referring to our invention, while "Pareto" is used when discussing the general mathematical notion of Pareto-optimality.

According to one aspect of the present invention there is provided a radiation therapy optimization method for a multi-objective optimization problem comprising a planning-target-volume surrounded by organs-at-risk in a patient to be treated using radiation, the method comprising:

representing computed tomography data of the patient as a three-dimensional grid of coordinates divided into voxels which contain the planning-target-volume and the organs-at-risk;

using a multi-objective optimizer to search successive generations of trial solutions to generate a database of optimized solutions that form a Pareto non-dominated set of solutions, which sample an estimation of a Pareto front to the multi-objective optimization problem where all solutions on the Pareto front are regarded as equally optimal, each trial solution being specified by a set of parameters defining beam orientations and fluence patterns which together define the radiation;

evaluating each generation of trial solutions by:
  estimating a radiation dose proxy to each voxel for each trial solution to the multi-objective optimization problem;
  associating a fitness function with each of the organs-at risk and the planning-target-volume;
  calculating a set of fitness values for each trial solution by evaluating the fitness functions associated with the trial solution using the respective radiation dose proxies of the respective voxels associated with the trial solution such that the fitness values are optimized with respect to Pareto-optimality of the trial solutions; and
  determining the Pareto non-dominated set of solutions to be optimized solutions by comparing the fitness values of the trial solutions to one another and to the fitness values of the optimized solutions of previous generations of the trial solutions;

continuing to generate successive generations of the trial solutions according to a defined convergence criterion until the optimized solutions are determined according to prescribed criteria to be sufficiently approximate Pareto-optimal solutions to the multi-objective optimization problem; and displaying the Pareto non-dominated set of solutions to a user by means of an interactive graphical interface.

PARETO is a software product that represents an advance in radiotherapy treatment planning. Current approaches to radiotherapy cancer treatment planning involve the manual selection and optimization of beam angles to deliver the prescribed radiation dose to a tumour while minimizing the dose to healthy OARs. This is an inefficient, time-consuming process, which does not necessarily result in truly optimal treatment plans. PARETO represents a novel use of the Ferret Genetic Algorithm, which automatically generates a large database typically containing several hundred to several thousand optimized solutions that represent the best possible set of trade-offs between competing treatment objectives for the PTV and all OARs. After optimization, the clinical user operates a visualization tool built in to PARETO to navigate this database of Pareto non-dominated solutions to select the best treatment option for the individual patient. The software decreases the human operator time required to generate treatment plans, while also resulting in superior radiotherapy treatment plans for the patient.

PARETO uses the Ferret Genetic Algorithm as its optimization engine. Ferret is a parallel linkage-learning genetic algorithm with unique machine-learning capabilities that allow it to efficiently solve difficult, large-scale, multi-objective optimization problems with many parameters. Ferret is considered a separate software product proprietary to nQube Technical Computing Corporation, which maintains an arm's length relationship with the invention described herein. PARETO and Ferret are compatible software products, but they are completely separate within the computer's file system and are distributed separately. In principle, PARETO could use any sufficiently powerful multi-objective optimizer, but Ferret is a natural choice for this project because it is powerful, parallel, and readily available due to the involvement of Ferret's creator (J. Fiege) in the project.

The problems of beam-angle selection and fluence pattern design in cancer radiotherapy treatment planning are multi-objective optimization problems, where the objectives are to simultaneously minimize the radiation dose to each nearby OAR of radiation damage when the prescribed radiation dose is delivered to the tumour, also termed the PTV. In general, it is not mathematically possible to identify a single "best" solution to such a problem, since compromises must be made between competing objectives. Rather, the problem is solved by finding a representative set of Pareto non-dominated solutions, which represent the optimal known trade-off solutions according to the defined objective functions. In this case, a Pareto non-dominated solution is given by a set of beam angles, as well as a set of parameters describing optimized fluence patterns of the radiation beams. These fluence patterns represent the fluence patterns to be delivered to the patient using intensity modulated radiation therapy (IMRT). A densely sampled database of Pareto non-dominated solutions approximates the mathematical Pareto front, thereby solving the treatment planning problem.

The treatment optimization problem requires parameters that represent both beam orientations and the spatial distribution of fluence at each beam angle. PARETO is primarily concerned with finding optimal beam angles, but this is not possible without simultaneously optimizing the fluence pattern. PARETO optimizes beam orientation parameters (gantry and couch angles) and fluence maps simultaneously as a single monolithic optimization problem, with both types of parameters handled identically by the optimizer.

PARETO automatically generates a database of Pareto non-dominated treatment plans for each patient, which represents the optimal set of compromises that could be used to treat the patient. Each plan is specified by a large number of parameters. For example, our simplest formulation using a single linear gradient and an OAR dose reduction method requires three parameters for each beam angle to model the gradient function, and one additional parameter is required for each OAR. Thus, $(3+N_{OAR})*N_{beam}$ parameters are required to model the fluence pattern, where $N_{OAR}$ is the number of OARs and $N_{beam}$ is the number of beams. The total number of parameters, including beam angles, is given by $N_{par}=(4+N_{OAR})*N_{beam}$ for coplanar beam angle optimizations, and $N_{par}=(5+N_{OAR})*N_{beam}$ for non-coplanar runs. Thirty-five parameters are therefore required for a five beam coplanar problem with three OARs.

PARETO must calculate the radiation dose throughout the patient in order to evaluate the fitness functions required by the optimizer. PARETO calculates radiation dose using an efficient ray-tracing algorithm that contains a novel feature to rapidly estimate exponential attenuation of the radiation beam. The ray-tracing procedure optionally makes use of hardware acceleration provided by multiple Graphics Processor Units (GPUs). Dose calculation convolves the primary dose with a realistic three-dimensional point-interaction dose scattering kernel to simulate the effect of photon scattering on the radiation distribution.

A fluence modulation procedure is applied to all regions of the PTV plus a margin visible in the "beam's eye view" (BEV) plane. We test PARETO using a geometry where the BEV plane is located 25 cm from the isocentre of the linear accelerator and 75 cm from the radiation source. Fluence patterns can be modeled by any method that represents the fluence spatial distribution by a set of parameters, which are controlled by the Ferret Genetic Algorithm. Several methods that have been successfully implemented and tested with PARETO include linear gradients, cosine transforms, beam groups, and isodose contours as described in the Detailed Description.

An additional visualization component of the software allows a clinical user to intuitively navigate this database to select one of the pre-optimized solutions that represents the most appropriate treatment plan for an individual patient. The visualization tool contains the following algorithms for Pareto-navigation:

1. A clustering algorithm designed to discover distinct families of solutions in the parameter space.
2. A comprehensive system for viewing solutions selected from a multi-objective "spoke plot".
3. A comprehensive system for viewing solutions selected from a set of overlain Dose Volume Histogram (DVH) plots.
4. A technique for limiting user solution exploration to sub-regions along each "spoke".
5. An algorithm for ensuring smooth transitions in display between solutions contained within the PARETO optimal database.
6. A technique for "short-listing" solutions of interest.
7. An active display of dose-volume histograms.
8. "Ghosting" of previously viewed solutions by displaying a faint representation of DVH curves corresponding to previously viewed solutions overlaid on the currently selected solution, for rapid and intuitive comparison with previously viewed solutions (TED).
9. Active three-plane view of radiation dose pattern for the treatment solution overlaid on patient computed tomography dataset, with all Regions of Interest (ROIs) displayed.

A second tool accepts user-defined weights, for objectives in the treatment plan, required by commercial radiation treatment planning systems and uses this information to select an approximately equivalent solution from our Pareto non-dominated set. This is useful for validating our fluence maps against those calculated by commercial planning systems for fixed beam angles.

PARETO is the only software package in existence that automatically solves the problem of beam angle selection and fluence optimization as a monolithic multi-objective optimization problem, in which the optimizer treats beam angle parameters and fluence parameters identically. This technique requires a powerful optimizer and an efficient mathematical representation of fluence maps, which is accomplished by the several methods described above and in the Detailed Description.

PARETO contains a novel algorithm for recursively merging beams that are closer than a small angle specified by the user (usually 10 to 15 degrees). When beam merging is enabled, PARETO's fitness functions prefer treatment plans requiring fewer beams. This functionality allows PARETO to automatically find treatment plans requiring fewer beams, thus decreasing treatment time and associated costs.

We have discovered that our method often divides the Pareto non-dominated database of solutions into well-defined classes or families of solutions, which are characterized by islands of solutions with similar beam orientations.

This classification is made possible by a novel use of a special feature of the Ferret Genetic Algorithm: Ferret allows PARETO to sort beams by gantry angle, and reinsert them into the genetic algorithm population in order of increasing angle. This procedure maintains the internal definition of each beam angle parameter, such that parameter-1 always refers to the lowest gantry angle, parameter-2 the second lowest, etc., which allows families of solutions to be seen clearly in projections of the parameter space. This careful sorting of angles also decreases the number of genetic algorithm "lethals" (poor quality solutions formed by combining two high-quality parent solutions), which improves the efficiency of the search.

PARETO therefore uses the Ferret Genetic Algorithm in a novel way, which sometimes results in the automatic discovery of classes or families of Pareto-optimal solutions of similar geometry. This provides an automatic method of classification, which organizes the space of solutions. Thus, an optimized PARETO database of solutions, which may contain thousands of solutions, can be represented within the visualization tool by showing a single representative solution chosen from each distinct family that is automatically discovered within the optimal set. Fine-tuning of solutions can be accomplished using PARETO's built-in interface for visualization and parameter space navigation.

PARETO represents a significant improvement over existing techniques for the following reasons:

1. The burden on the clinical user is dramatically reduced. Rather than iteratively optimizing a treatment plan by hand, the user scans through a set of pre-optimized treatment plan solutions using a graphical database navigation tool and selects the best treatment plan for the patient. The software's automation does not replace the expertise of a clinician; rather it allows him or her to apply his or her expertise more effectively and much more rapidly.
2. PARETO can be configured to automatically minimize the number of beam orientations required, thus reducing treatment time and associated costs.
3. PARETO finds and displays multiple families of solutions, which represent qualitatively different radiation treatment plans. Non-obvious beam arrangements are frequently discovered, which may provide novel treatment alternatives for the clinical user to consider.
4. All solutions found by the software are highly optimized treatment plans that span a trade-off surface. This is in contrast to treatment plans produced manually, which may be far from optimal. Solutions selected from our Pareto-optimal database by a clinician are demonstrably superior to manual plans, based on quantitative dose-volume histograms. This is expected to decrease radiation-induced complications and improve treatment outcomes for patients.
5. By significantly decreasing the time spent by an expert human operator to develop a customized treatment plan, the software will decrease the overall cost of treatment per patient, while also increasing the number of patients that can be treated by cancer treatment centres.

PARETO is the only software product in existence that solves the multi-objective problems of beam angle selection and beam fluence modulation in radiotherapy, in a multi-objective framework. This is known to be a difficult non-convex problem that cannot be solved by most optimization methods. The unique mathematical innovations within the software allow it to successfully optimize these difficult problems.

PARETO separates the treatment planning process into an automated optimization problem, and an interactive stage in which a human expert uses a graphical navigation tool to select a treatment plan from the Pareto-optimal set. In this sense, PARETO can be regarded as the next stage in computer-aided radiotherapy treatment planning. Pareto-navigation is made efficient by PARETO's automatic classification of treatment options, combined with an intuitive user interface.

PARETO's ability to automatically find distinct families of solutions is a unique property of the software, and a novel use of a feature that is built into the Ferret optimizer. This feature allows PARETO to automatically discover and classify novel treatment geometries.

PARETO's efficient representations of the fluence patterns are non-obvious methods that make the code well suited to use a genetic algorithm as its optimization engine. A related non-obvious feature of the software is its ability to handle the problems of beam angle selection and fluence modulation as a single, monolithic optimization problem, in which the same optimizer handles the beam angle parameters and fluence parameters simultaneously and in an identical fashion.

PARETO's fluence representation can be easily modified to use parameterizations other than those presently included with the software if needed. Methods providing a high degree of modulation with a low number of parameters are most desirable.

PARETO's dose calculation method affects achievable accuracy in calculated patient doses but does not affect the manner in which PARETO achieves multi-objective optimization solutions. The dose calculation method used currently can be replaced with any other patient dose calculation method for increased accuracy or efficiency.

PARETO can be used to optimize beam orientations and fluence patterns in stereotactic radiosurgery, without significant modification.

PARETO could be modified to optimize arc angle selection and intensity modulation in single-arc therapy (often described as volumetric modulated arc therapy, or VMAT), since this treatment methodology involves nearly the same optimization problem applied to a different delivery geometry.

The software will first appear in clinical use as a "treatment advisor" tool, which will help users to select optimized beam angles for final clinical evaluation using existing commercial treatment planning tools. We expect that the software will subsequently evolve into a complete stand-alone treatment planning system with powerful optimization capabilities not found in any other commercial software.

Radiotherapy is delivered to most cancer patients as a key component of their treatment plans, which may also include surgery and chemotherapy. Radiotherapy is a mature and very heavily researched field, with a significant number of publications focusing on the optimization of fluence patterns. However, few contributions address the more difficult, but equally important problem of beam angle selection. Even fewer publications address the multi-objective nature of the radiotherapy optimization problem.

Current treatment planning techniques require iterative manually guided optimization by an experienced technician. Our software fundamentally transforms this tedious process into a rapid search through a pre-optimized set of solutions. We expect about an order of magnitude reduction in the total human planning time that is required per patient and related cost savings to health care. Moreover, standard dose-volume histograms, used to evaluate radiation treatment plans, show that our software typically results in a dosimetrically significant reduction in the radiation dose to critical structures.

Halabi, Craft, and Bortfeld (Phys. Med. Biol., 51:3809-3818, 2006) have recently developed a mixed integer programming approach for the multi-objective optimization of IMRT beamlet intensities without beam angle optimization. This software solves the fluence optimization problem, but not the problem of beam angle selection. Although their research is related to ours, we do not regard their approach as competitive because they use a fundamentally different optimization approach wherein the mathematics employed are unable to handle non-convex problems, and are therefore insufficient to optimize beam orientations.

The visualization and Pareto-navigation component of our software is functionally similar to the MIRA software discussed by Monz, et al (Phys. Med. Biol. 53:985-998, 2008). However, they focus on visualization without actually solving the optimization problem, and we include additional methods to select DVH curves directly. Our visualization software is only one component of an integrated package that solves the full problem of beam angle optimization, fluence optimization, and Pareto solution navigation. In addition, our visualization software simplifies Pareto-navigation by making used of the clustered nature of the solutions discovered by PARETO. There is no analogous capability in MIRA, or any other software product that we are aware of.

Referring now more particularly to the method aspect of the present invention defined above, preferably the set of parameters defining the radiation of each trial solution includes beam orientations and fluence patterns for each one of a number of beams of radiation.

The method preferably includes prompting the user to select a maximum number of beams of radiation to be used by the optimizer to define the radiation of each trial solution.

The number of beams of radiation is preferably also optimized.

In some instances first beams closer than a certain minimum angle are merged together to form a single beam at an intermediate angle defined by fluence parameters constructed by averaging together the parameters of the first beams.

A penalty function may be defined to prefer solutions requiring a fewer number of beams.

Beams may be sorted by gantry angle, thus rearranging the order of their defining parameters, and re-inserted into the genetic algorithm population.

Size of the parameter space may be reduced by sorting beams by gantry angle.

Preferably beam averaging is applied recursively.

Beam angles for a trial solution may be placed in ascending order of gantry angle and re-inserted into a genetic algorithm population in order to reduce the size of a respective parameter space.

Preferably a linkage learning algorithm of a genetic algorithm is applied to beam angle parameters but not fluence parameters.

The fluence pattern for each beam may be represented:
 by a linear gradient that is thresholded such that the fluence is greater than or equal to zero;
 by a linear gradient that is thresholded such that the fluence is greater than or equal to zero and less than or equal to one; or
 by a sum of linear gradients with the fluence thresholded such that the fluence is greater than or equal to zero and less than or equal to one;
  wherein each linear gradient comprising the sum is thresholded such that the fluence is greater than or equal to zero; or
 each linear gradient comprising the sum is thresholded such that the fluence is greater than or equal to zero and less than or equal to one.

Preferably the number of coefficients of a discrete cosine transform is increased dynamically during a run to increase fluence modulation.

The fluence pattern for each beam may be represented by two-dimensional interpolation from a square grid of pencil beam groups dividing each beam.

Preferably the number of beam groups is increased dynamically during a run to increase fluence modulation.

The fluence pattern for each beam may be represented by the coefficients of a discrete cosine transform using only low frequency terms.

Preferably the number of coefficients of a discrete cosine transform is increased dynamically during a run to increase fluence modulation.

The fluence pattern for each beam may be represented by several apertures of variable intensity with shapes defined by a projection of isodose surfaces calculated from a plan with equally weighted conformal fields onto a beam's-eye-view plane Preferably the fluence patterns are applied over each OAR for each beam to modulate the rays that intersect with the OARs.

Preferably a fluence reduction parameter q is defined for each OAR for each beam to reduce the fluence on rays that intersect with OARs by the equation $$F_{OAR} = qF_{PTV}; q \in [0,1],$$

where $F_{PTV}$ represents the fluence that would have passed through the PTV in the absence of the fluence reduction parameter.

Fluence for each beam over a variable PTV margin size is preferably defined by a parameter that is optimized during the run according to the fitness functions such that the fluence is zero external to the margin.

The method may further include rejecting beam orientations that cannot be realized by treatment hardware by setting all fitness values to a large number that increases with the degree to which hardware constraints are violated.

The method may also include estimating the radiation dose proxy to each voxel by using rays in a ray-tracing algorithm to determine which voxels are intersected by each beam.

Preferably a compact approximation of the exponential function is used to estimate the exponential function to calculated radiation intensities.

The method may also include computing a fluence pattern using fluence parameters received by the respective fitness function and modulating each ray intersecting the planning-target-volume and its margin by the computed fluence pattern.

The exponential attenuation and an inverse-square law effect on the primary radiation fluence may also be computed to determine the total energy released per unit mass for each voxel.

Preferably a convolution of the terma distribution is performed with a scattering kernel arranged to simulate an effect of scattering on radiation distribution to determine the radiation dose proxy.

Preferably the method also includes specifying an organ type for each organ-at-risk and associating a fitness function with each organ-at-risk based on the specified organ type.

A simple volumetric fitness function for volumetric organs-at-risk may be defined by the following equation:

$$F_{OAR,VOL} = \frac{N_{OAR,i}^{-1} \sum_{i=1}^{N} D_{OAR,i}}{M^{-1} \sum_{i=1}^{M} D_{PTV,i}}$$

representing the mean organ-at-risk dose, normalized to mean PTV dose, where $D_{OAR,i}$ and $D_{PTV,i}$ are OAR and PTV dose respectively; and N and M are the number of OAR and PTV voxels respectively.

A simple serial fitness function for serial organs-at-risk may be defined by the following equation:

$$F_{OAR,SER} = \frac{\max(D_{OAR})}{M^{-1} \sum_{i=1}^{M} D_{PTV,i}}$$

representing the maximum organ-at-risk dose, normalized to mean PTV dose, where $\max(D_{OAR})$ is OAR dose maximized over all OAR voxels; $D_{PTV,i}$ is PTV dose applied to voxel i; and M is the number of PTV voxels.

A DVH fitness function for volumetric or serial organs-at-risk may be defined by the following equation:

$$F_{OAR} = \frac{1}{V_{OAR}} \left[ \sum_{i=1}^{N} f_i^P \Delta V_{OAR,i} \right]^{\frac{1}{p}}; f_i \equiv \left\{ \begin{array}{ll} 0, & D_i \leq D_0 \\ D_i / D_0, & D_i > D_0 \end{array} \right\}$$

representing the volume-weighted mean thresholded dose computed from a dose-volume histogram (DVH) with N bins, where $\Delta V_{OAR,i}$ is the increment in volume from the i'th bin of the DVH and $V_{OAR}$ is the total volume; $D_i$ is dose associated with DVH bin i; and $D_0$ is the target dose threshold for the OAR; such that voxels receiving the highest dose are more strongly suppressed for larger values of exponent $p \geq 1$; where a value of $p=1$ is appropriate for volumetric structures, while $p>1$ is appropriate for serial structures.

An EUD fitness function for volumetric or serial organs-at-risk may be defined by the following equation:

$$F_{EUD} = \left( \sum_{i=1}^{N} f_i^p \right)^{\frac{1}{p}}; f_i \equiv \left\{ \begin{array}{ll} 0, & D_i \leq D_0 \\ D_i / D_0, & D_i > D_0 \end{array} \right\}$$

representing the equivalent uniform dose with dose threshold $D_0$, where $D_i$ is dose applied to voxel i; $D_0$ is the target dose threshold for the OAR; N is the number of OAR and PTV voxels, respectively; where exponent $p=1$ best corresponds to volumetric structures and values of $p>1$ are most appropriate for serial structures.

A conformity fitness function of the planning-target-volume may be defined by the following equation:

$$F_{PTV} = \log_{10} \left\{ \frac{1}{2} \left[ 1 - \frac{\sum_{i=1}^{N} Q_i (D_i - \overline{D})(M_i - \overline{M})}{\sigma_D \sigma_M} \right] \right\}$$

-continued $$\sigma_D = \left(\frac{\sum_{i=1}^{N} Q_i(D_i - \overline{D})^2}{\sum_{i=1}^{N} Q_i}\right)^{\frac{1}{2}} \sigma_M = \left(\frac{\sum_{i=1}^{N} Q_i(M_i - \overline{M})^2}{\sum_{i=1}^{N} Q_i}\right)^{\frac{1}{2}}$$

wherein the conformity fitness function is based on a statistical correlation function between a dose proxy matrix D and a planning-target-volume mask M, where M is defined such that a value of 1 is assigned to all voxels inside the PTV and 0 outside; $\sigma_D$ and $\sigma_M$ are the weighted dose and mask standard deviations, respectively; N is the total number of voxels inside the patient volume; and weight matrix Q determines the relative weight applied interior and exterior to the PTV.

A standard deviation fitness function of the planning-target-volume may be defined by the following equation:

$$F_{PTV} = \frac{\left[\sum_{i=1}^{M}(D_i - \overline{D})^2\right]^{\frac{1}{2}}}{\sum_{i=1}^{M} D_{PTV,i}}$$

where $D_i$ is dose applied to voxel i, $D_0$ is the target dose threshold for the OAR, and M represents the number of PTV voxels.

A hot zone may be defined as the set of voxels near the PTV such that $d_i \le f_{PTV}*d_{PTV}$ where $d_i$ is the distance from voxel i to the nearest voxel within the PTV; $f_{PTV}$ is a fractional value less than or equal to 0.5; and $d_{PTV}$ is the maximum distance between voxels within the PTV.

A cool zone may also be defined as the set of voxels outside the hot zone and within the patient skin.

A penalty function to suppress radiation hotspots may be defined by the equation:

$$F_{penalty}* = F_0*(1+\max\{d_i/d_0 | d_i > f_{PTV}*d_{PTV} \text{ and } D_i > D_{OHT}, i \in \{1 \ldots N\}\})$$

where $d_i$ is the distance from voxel i within the treatment volume to the nearest voxel within the PTV structure; $d_0$ is the maximum value of $d_i$ over all voxels in the treatment volume; $f_{PTV}$ is a fractional value less than or equal to 0.5; $d_{PTV}$ is the maximum distance between voxels within the PTV, such that the product $f_{PTV}*d_{PTV}$ defines the size of the allowed hot zone near the PTV; $D_i$ is the dose received by voxel i; $D_{OHT}$ is the maximum desired dose to other healthy tissue outside the hot zone; and N is the number of voxels within the treatment volume.

The penalty function to suppress radiation hotspots may also be defined by the equation:

$$\text{dose\_violation} = \max\left\{0, \left(\frac{D_i - D_{OHT}}{D_{OHT}}\right)\right\} \forall i \in \{1 \ldots N\} | d_i > f_{PTV}*d_{PTV}$$

$$F_{penalty} = \begin{cases} 0, & \text{if dose\_violation} = 0 \\ F_0 + \text{dose\_violation}, & \text{if dose\_violation} > 0 \end{cases}$$

where $d_i$ is the distance from voxel i within the treatment volume to the nearest voxel within the PTV structure; $d_0$ is the maximum value of $d_i$ over all voxels in the treatment volume; $f_{PTV}$ is a fractional value less than or equal to 0.5; $d_{PTV}$ is the maximum distance between voxels within the PTV, such that the product $f_{PTV}*d_{PTV}$ defines the size of the allowed hot zone near the PTV; $D_i$ is the dose received by voxel i; $D_{OHT}$ is the maximum desired dose to other healthy tissue outside the hot zone; and N is the number of voxels within the treatment volume.

Preferably the weight matrix Q is set equal to zero within voxels within the cool zone.

Distance $d_i$ can be calculated exactly, or rapidly estimated according to the following procedure:

defining n to be an integer greater than approximately 25;
defining a matrix R of radii such that $R=[(X-x_0)^2+(Y-y_0)^2+(Z-z_0)^2]^{1/2}$
where X, Y, and Z are matrices of Cartesian coordinate values for the voxels constructed from coordinate vectors x, y, and z; and $x_0$, $y_0$, and $z_0$ are the coordinates of a central voxel such that $x_0=x(\text{floor}((Nx/2)+1))$, $y_0=x(\text{floor}((Ny/2)+1))$, and $z_0=z(\text{floor}((Nz/2)+1))$ where Nx, Ny, and Ny are the lengths of coordinate vectors x, y, and z respectively;
redefining values of R equal to zero to be equal to the smallest non-zero value of R; and
calculating a matrix of distances $d=\{d_i\}$ by performing the convolution: $d=[\text{conv}(M, R^{-n})]^{-1/n}$.

In some embodiments the set of parameters defining the radiation of each trial solution may include dose rate, gantry rotational speed, and multi-leaf collimator positions for volumetric modulated arc therapy.

In further embodiments the set of parameters defining the radiation of each trial solution may include dose rate, parameters defining the orientation of non-coplanar arcs, beam directions, and aperture shape for volumetric modulated arc therapy.

Alternatively the set of parameters defining the radiation of each trial solution may include dose rate, non-coplanar arcs, beam directions, and aperture shape for stereotactic radiosurgery.

Preferably all parameters defining the radiation and the fitness functions together comprise a single monolithic optimization problem in which all parameters are treated identically and varied simultaneously by the optimizer to optimize the fitness functions.

The method may also include displaying radiation dose patterns and dose volume histograms of selected solutions of the Pareto non-dominated set of solutions to the user.

The fitness values of each solution may be represented as polygons on a respective spoke plot in which each spoke represents a normalized objective of the multi-objective optimization problem with optimal fitness values towards a centre of the plot.

The user may be assisted to select a final treatment solution from the Pareto non-dominated set of solutions to treat the patient by allowing graphical comparison between the Pareto-non-dominated set of solutions.

The method may also include filtering Pareto non-dominated set of solutions for display by defining maximum and/or minimum dose constraints.

Preferably short-listed solutions are displayed overlaid on one-another for comparison purposes.

A clustering algorithm may be used to discover distinct families of solutions in the parameter space.

A comprehensive user interactive system may be used for viewing solutions selected from a multi-objective spoke plot wherein each Pareto non-dominated solution is represented as a polygon connecting spokes. The method in this instance may include limiting user solution exploration to sub-regions along each spoke.

A comprehensive user interactive system may also be used for viewing solutions selected from a set of displayed DVH curves representing the Pareto non-dominated set.

Preferably an algorithm is used for ensuring smooth transitions in solution display along the Pareto front.

A technique is also preferably provided for a user to short-list solutions of interest.

The method may further include an active display of dose-volume histograms.

Previously viewed solutions may be ghosted for rapid and intuitive comparison with previously viewed solutions.

An active 3-plane view of radiation dose pattern may be provided for the treatment solution overlaid on patient computed tomography dataset, with all regions-of-interest displayed.

Preferably the prescribed criteria of the method for determining the optimized solutions to be a set of converged Pareto non-dominated solutions comprises no fitness values being improved by a prescribed amount in a prescribed number of previous generations of trial solutions.

One embodiment of the invention will now be described in conjunction with the accompanying drawings in which:

DETAILED DESCRIPTION

Figure 1:
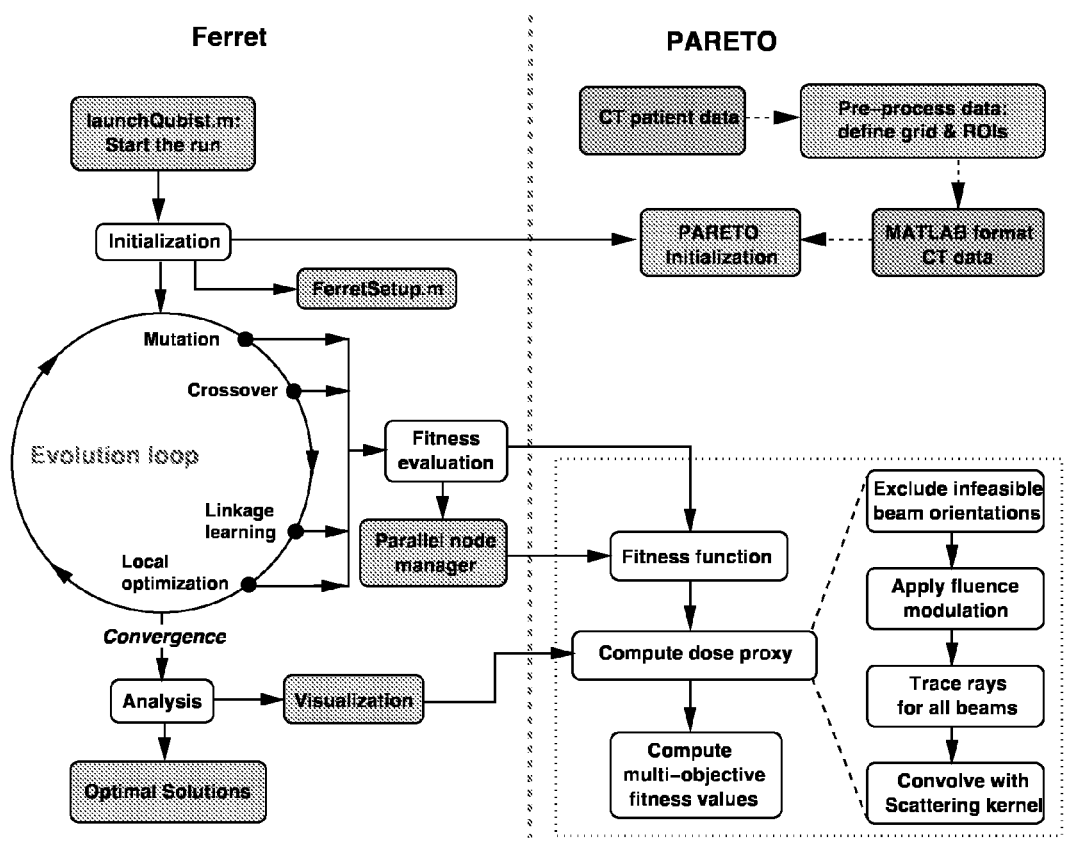
FIG. 1 is a Flowchart showing the separation (red-dashed line) between Ferret and PARETO, and the interaction between these two separate software packages in which solid flowchart arrows indicate one function calling another and the dashed arrows represent the flow of information when loading patient data.

The flowchart (FIG. 1) shows the separation (red-dashed line) between the Ferret Genetic Algorithm and PARETO, and the interaction between these two separate software packages. Solid flowchart arrows indicate one function calling another. The dashed arrow represents the flow of information when loading patient data.

Ferret is a publicly available multi-objective genetic algorithm, which was developed by one of PARETO's inventors (J. Fiege). It is a component of the Qubist Global Optimization Toolbox for MATLAB, which is distributed by nQube Technical Computing Corporation (Winnipeg Manitoba, www.nqube.ca). Ferret is a powerful and general-purpose multi-objective optimizer, which optimizes a fitness function (or multiple fitness functions) defined by the user, such as the PARETO fitness function shown on the right hand side of the diagram. It is an important point that PARETO could make use of a different sufficiently powerful optimizer in principle, but it is convenient to use Ferret because of J. Fiege's involvement with the project.

Ferret's optimization engine is controlled by a general graphical user interface, which is used to load projects, monitor their progress, analyze results, and visualize solution sets. Use of the Ferret graphical interface is optional, but it currently serves as the graphical "front end" used to control PARETO runs. Ferret is distributed with source code defining the graphical interface, which can be freely modified by the user; thus future versions of PARETO will include a customized interface specific to the software.

1. Procedure to Run PARETO

The steps to run PARETO are as follows:

1. Computed Tomography (CT) patient data is assumed to be stored on the user's file system, and can be converted into a representation of densities through a standard phantom calibration procedure. Radiotherapy structures are also loaded in, and contours defined representing various regions of interest within the CT dataset, for example the tumour tissues and OARs such as spinal cord, parotid glands, rectum, etc.

2. A pre-processing program reads the patient's CT data and contoured structure data from the file system. The three-dimensional grid of coordinates is defined and divided into voxels (three-dimensional pixels). Structure data is converted to "masks", specifying voxels containing all regions of interest (ROIs), including the PTV and all OARs. The CT data is converted to a three-dimensional array of linear attenuation coefficient data. These data structures are saved to disk using MATLAB's internal .mat file format.

3. Ferret is launched within MATLAB using the standard "launchQubist" command, which is part of the Qubist optimization toolbox, which contains the Ferret Genetic Algorithm. A section of the launchQubist.m program that is intended to be altered by the user is modified to contain the location of the PARETO project on the computer's file system and other information about PARETO's initialization and setup procedure, which allows PARETO to be initiated by selecting it from Ferret's "Projects" menu.

4. The previous step triggers Ferret's initialization procedure. Ferret's initialization calls PARETO's own initialization function, which loads pre-processed data from the computer's file system.

5. The FerretSetup.m file is a standard Qubist file, which is intended to be modified by the user to configure the Ferret Genetic Algorithm. The FerretSetup.m file is read, which specifies the options that are to be used by Ferret during the run. Some of these options are described in the Qubist User's Guide. Other customizations define PARETO's parameters and other quantities required by PARETO.

6. Ferret begins its evolution loop, which cycles through the set of genetic operators used by Ferret to optimize PARETO's fitness functions. Several of the most important operators are shown on the flowchart, but the reader is referred to the Qubist User's Guide for a more complete description.

7. Each Ferret generation (cycle of the evolution loop) requires numerous evaluations of the PARETO fitness functions, at several points during the cycle. In general, the number of evaluations required during each generation is comparable to the genetic algorithm population size. Fitness evaluation may occur either by directly calling the PARETO fitness function, or evaluation may be called by the parallel node manager, which is a component of the Qubist global optimization toolbox. Ferret is a parallel algorithm, which allows multiple CPUs (either in the same multi-CPU computer, or in a cluster of computers with a shared file system) to work together, in order to optimize the fitness function more rapidly than can be accomplished by a single CPU. The parallel node manager allows the user to specify the number of CPUs (nodes) to be used for the run, and both start and stop nodes.

8. The PARETO fitness function accepts a set of beam angles and other parameters specifying the fluence map for each beam, plus the patient data loaded during initialization. Ultimately, this input is used to generate a fitness value for each objective function, which is returned to Ferret for optimization. This is accomplished by the following steps:

8a. Beam orientations that cannot be realized by the treatment hardware (infeasible orientations) are rejected. This is done by returning a large value for all fitness functions, where the value is determined by an algorithm, such that the fitness value increases with the degree of constraint violation. Note that Ferret is a minimizer, so that large fitness values correspond to poor solutions that will be rejects in subsequent generations.

8b. If the beam orientation is not rejected in step 8a, a fluence pattern is computed for each beam using the fluence parameters received by the fitness function. This fluence pattern is transported through the patient model for each beam, and resulting radiation dose is calculated as in 8c to 8d.

8c. A ray tracing algorithm is used to determine which target voxels are intersected by each beam. Fluence that does not pass through the PTV is turned off. Photon attenuation and the inverse square law (for intensity fall-off away from a point source) are taken into account in the fluence calculation. Divergent beam geometry is used.

8d. The three-dimensional fluence is convolved with a three-dimensional point-interaction dose scattering kernel to simulate the effect of photon scattering on the radiation distribution. The result is a three-dimensional matrix labeled as the radiation dose proxy on the flowchart.

8e. PARETO uses the dose proxy matrix to calculate a set of multi-objective fitness functions, which are sent back to Ferret, either directly or via the Qubist node manager. In general, there is one fitness function per OAR, plus an additional fitness function for the PTV. Penalty function may be added to the fitness functions to prefer solutions requiring fewer beams or to suppress dose hotspots distant from the PTV. The hotspot penalty function evaluates to zero and does not affect the fitness functions if no hotspots are present.

9. Ferret continues cycling through the evolution loop, and improves the set of solutions present in the genetic algorithm population at each generation (cycle). Ferret populates the Pareto non-dominated set (or trade-off surface) with solutions, which are saved to disk in Ferret "History" files.

10. Ferret exits when convergence is detected by PARETO's stopping criterion. The stopping criterion can be modified by the user, but a typical configuration would stop the code when no fitness function has improved by more than 1-3% for the previous 100 generations. Runs can also be stopped manually when the solution database is judged to contain a sufficient number of solutions of adequate quality.

11. Ferret's analysis method is used to load the History files that have been saved to disk, and construct the final optimal set, which is a standard data structure defined by Ferret and called "OptimalSolutions". This is done by comparing solutions that were considered optimal in their own generation, with solutions considered optimal at other generations. A solution is discarded if it is discovered to be inferior (Pareto-dominated) by another solution. Generally, solutions found during later generations are superior to solutions from earlier generations. Many solutions saved in Ferret's History files are therefore discarded when the final Pareto-optimal set is computed. The OptimalSolutions structure contains all parameters and other information required to reconstruct any solution within the trade-off surface.

11. The optimal set is saved to the computer's file system as a MATLAB structure called OptimalSolutions.mat, which normally contains several thousand solutions that are equally good, in a multi-objective Pareto-optimal sense.

12. The solution set is visualized using Ferret's built-in visualization features.

Figure 2:
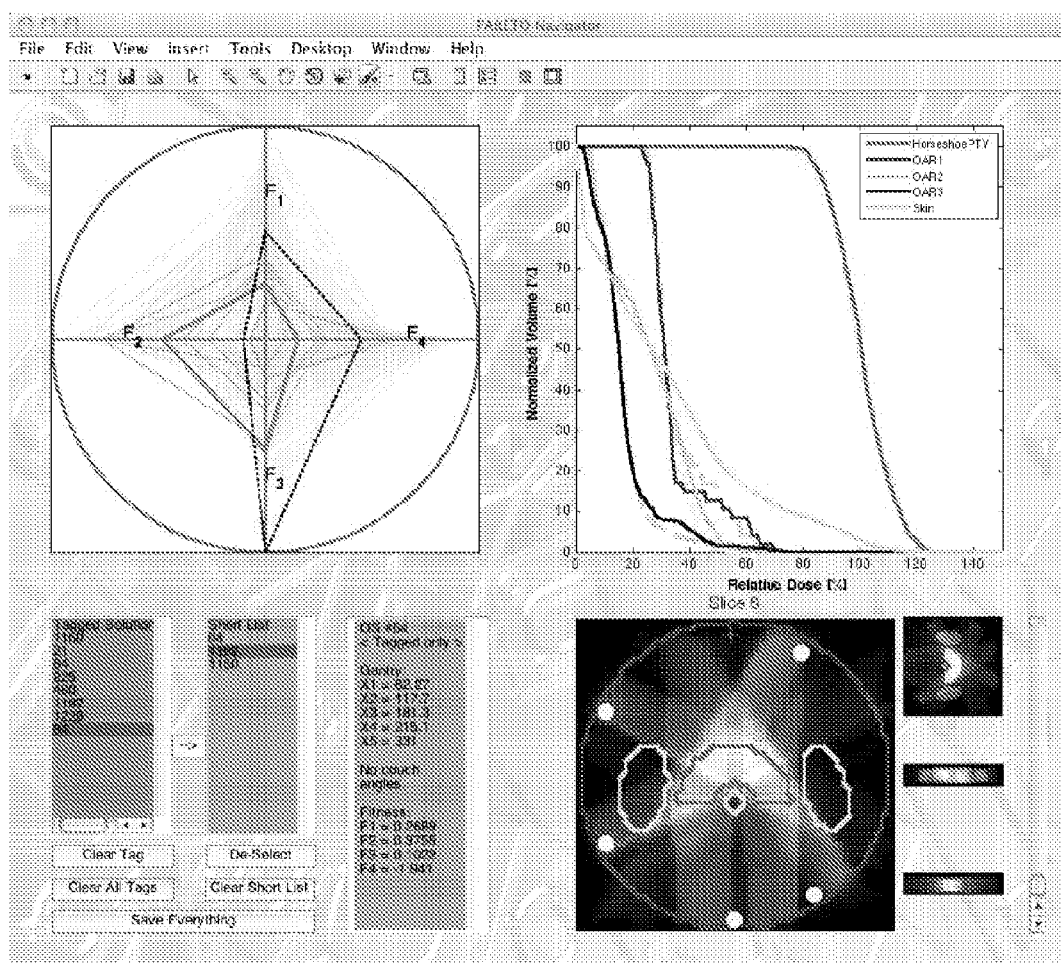
FIG. 2 is an image of the graphical user interface (the PARETO Navigator) used to explore the Pareto non-dominated database generated by a PARETO run, showing the software applied to an artificial data set that is referred to as the spinal phantom.

13 (not shown on flowchart). A treatment solution is selected by loading OptimalSolutions.mat into the PARETO Solution Navigator shown in FIG. 2. The Navigator is a customized interface specific to PARETO, which contains interactive graphical components designed to display the radiation dose pattern and dose volume histograms (DVHs) to the clinician. Fitness values are displayed as a polygon on an interactive "spoke plot" or an interactive DVH plot, which allows the user to visually evaluate the properties of each solution. Solutions of interest to the clinician are "short-listed" for final consideration. The user compares short-listed solutions, and finally chooses a pre-optimized plan to treat the patient.

The 'spoke plot' (shown on the upper left of FIG. 2) is the most important element of the visualization tool. Each spoke represents a normalized objective, with the best fitness values toward the centre, and a single solution is therefore represented by a polygon with a vertex for each objective. These polygons are highlighted by a black dashed line as the user hovers their mouse cursor over the figure. A related feature using a similar algorithm allows the use to select DVH curves from the set of DVH curves representing the optimal set. Interesting solutions are 'tagged' by clicking on the figure and appear in the text box in the lower left of the figure. The parameters and fitness values are shown in the gray text box, while the DVH curves and three different projected images of the solution are shown in the figures to the right. Solutions that have been previously tagged can be moved to the 'short-list' box and saved, along with all figures and parameter values. The small images on the right are active thumbnail images of three orthogonal CT image projections. When clicked, a larger version of the selected image appears in the axes to their immediate left. Different slices can be viewed by moving a slider component shown on the interface.

The DVH curves optionally make use of a novel feature called "ghosting", in which a faint image of DVH curves from previously selected solutions remains visible on the DVH plot when a new current solution is selected. The user defines the maximum number of solutions allowed to be shown simultaneously, such that DVH curves from more recently viewed solutions are more apparent than older solutions which are more faint. This feature allows easy comparison between the current solution and previously viewed solutions. An example of ghosting is visible on FIG. 2 as faint dashed gray lines. In this case, the ghosted solution was very similar to the current solution, causing the ghosted solution to be mostly obscured by overlapping DVH curves from the current solution. This example illustrates the utility of ghosting to illuminate subtle differences a pair of similar solutions.

Figure 3:
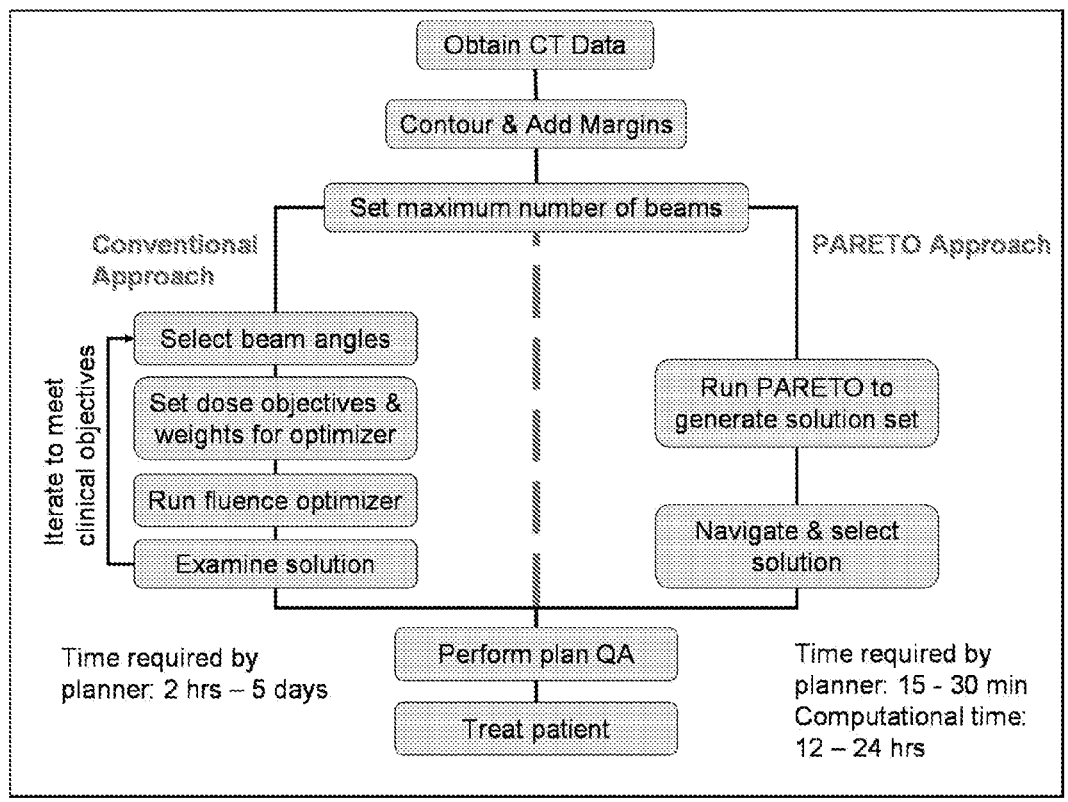
FIG. 3 is a flowchart contrasting the use of PARETO for radiotherapy treatment planning with the conventional method for radiotherapy planning.

2. The PARETO Process Compared to a Conventional Radiotherapy Optimization Process:

Conventional treatment planning for IMRT can be a very time consuming process, involving an iterative, manual trial-and-error approach lasting anywhere between 2 hrs to several days, as illustrated in FIG. 3. It is not likely that the final treatment plan is truly optimal since the number of iterations is limited by time constraints. Single-objective optimization strategies are employed that construct a single objective function by weighting together multiple objectives along with appropriate constraints; thus even a well-optimized plan is blind to other regions of the multi-objective trade-off surface unless weights and/or constraints are adjusted, which requires the entire solution to be recomputed from the start. Often the treatment planner (the human operator of this software) will require guidance from the radiation oncologist as to how they would like various critical structure compromises to be handled, which can add large amounts of time to the overall planning process. Furthermore, the quality of the final solution is heavily dependent on the experience and ability of the individual treatment planner developing the plan.

However, using PARETO, the human-guided iterative approach to treatment planning optimization is completely removed. Instead, the multi-objective Ferret Genetic Algorithm is used to automatically create a database of Pareto-optimal solutions for a patient. During the computation, the planner is free to work on other tasks. Once PARETO converges, a database of Pareto non-dominated solutions is stored and may be reviewed using either Ferret's standard visualization interface, or the PARETO Navigator interface. The Navigator GUI provides various tools to allow the planner or clinician to filter through and examine the optimal solutions, in order to choose the one that will provide the best care for the individual patient. The PARETO approach requires only approximately 5-15 min of the planner's time. Thus, compared to conventional treatment planning approaches, it saves considerable time for the human user, improves efficiency, and therefore reduces the cost of radiotherapy planning to the health care system.

Conventional Process:
1. Computed Tomography (CT) data of the patient is obtained and converted to density data.
2) Regions of interest (ROIs) defining the structures involved in the treatment plan are contoured and a margin added around the clinical target tissues to arrive at the PTV.
3) Dosimetric objectives are laid out by the clinician that are to be met by the treatment planner using a certain number of external beams.
4) An initial set of beam angles is set as picked by the treatment planner based on prior experience, a template from the commercial planning system, or by trial and error.
5) Objectives and objective weights are set by the treatment planner based on prior experience, a template from a commercial planning system, or by trial and error. These objectives and weights are intended to drive the fluence optimization to the clinical objective.
6) The planning system optimizes the fluence pattern (but not beam angles) using the conditions from steps 4 and 5.
7) The treatment planner examines the solution. The plan is reworked starting at step 4, if it does not meet dosimetric objectives laid out by the clinician. For complex patient treatments, several iterations are typically required.
8) The plan is evaluated in a quality assurance program. If rejected, the planner returns to step 4.
9) The patient is treated with the final plan.

PARETO Process:
1) Computed Tomography (CT) data of the patient is obtained and converted to density data.
2) Regions of interest (ROIs) defining the structures involved in the treatment plan are contoured and a margin added around the clinical target tissues to arrive at the PTV.
3) The user specifies the maximum number of beams. This allows PARETO to find solutions using a variable number of beams ranging between one and the maximum number of beams. Given a pair of solutions where neither is Pareto-dominated by the other according to the fitness functions, PARETO prefers the solution requiring a fewer number of beams. This is accomplished by means of a small penalty function that is added to the fitness functions such that the penalty increases with the number of beams employed.

4) The user selects a method for fluence modulation from the methods included with PARETO.

5) PARETO is allowed to run until it has converged, and a database of Pareto non-dominated optimal solutions is generated automatically. During this time the user is not required to be at the computer, and is therefore available to perform other tasks.

6) The user navigates the database of solutions using the PARETO Navigator graphical user interface, which allows pre-optimized solutions to be selected based on their dose distributions, isodose contours, and DVH curves. The user can also view and tag solutions, allowing multiple solutions to be viewed at once containing a dose volume histogram (DVH) and projections of the radiation through the patient. The expertise of an experienced planner is still required at this stage, but the process is rapid because all plans displayed are already guaranteed to be Pareto non-dominated, and are nearly Pareto-optimal in practice for a multitude of trade-offs; thus, PARETO eliminates the time-consuming human interaction required for optimization under conventional treatment planning.

7) The plan is evaluated for quality assurance. If rejected, the planner returns to step 6, and selects a different plan from the PARETO database.

8) If the planner determines that no adequate solution exists within the database of solutions, PARETO is re-run specifying a larger maximum number of beams and/or a different method for fluence modulations.

9) The patient is treated with the final plan.

3. Fluence Optimization

Fluence optimization is crucial to obtain realistic evaluations of the fitness functions for each beam angle. A fluence modulation procedure is applied to all regions of interest (ROIs, which includes the PTV and OARs) visible in the "beam's eye view" (BEV) plane. PARETO uses the set of fluence patterns to calculate an approximate dose distribution within a three-dimensional grid of voxels representing the patient. We test PARETO using a geometry where the BEV plane is located 25 cm from the isocentre of the linear accelerator and 75 cm from the radiation source.

Fluence patterns can be modeled by any method that represents fluence spatial distribution by a set of parameters. Several methods that have been successfully implemented and tested with PARETO include linear gradients, cosine transforms, beam groups, and isodose contours as described below. In each case, the fluence optimization is set up as part of a "monolithic" problem, such that Ferret optimizes beam angles and fluence patterns simultaneously. These alternate fluence parameterization methods are discussed below:

Linear Gradient Fluence Method:

The fluence pattern for each beam is generated by the following procedure:

1. Construct a set of linear gradient fluence patterns defined by the equation:

$$F_i = F_0 + [g \cdot (x - x_0)]$$

where $x=(x,y)$ defines the coordinates of the BEV; $g=(g_x, g_y)$ is the fluence gradient; $F_0$ is fluence offset; $x0$ is the centre of the PTV projected on the BEV plane; and $i \in \{1 \ldots N_{grad}\}$, where $N_{grad}$ is the number of gradients specified by the user's setup file.

2. Perform a lower truncation of each linear gradient fluence pattern according to the equation:

$$F_i = \max(0, F_i)$$

3. If the user's setup file specifies that upper truncation should be performed on each linear gradient fluence pattern prior to combining patterns, then truncate according to the equation:

$$F_i = \min(1, F_i).$$

4. Compute the combined fluence pattern by averaging over the individual linear gradients:

$$F = N_{grad}^{-1} \sum_{i=1}^{N_{grad}} F_i$$

5. Perform an upper and lower truncation of the summed fluence pattern:

$$F = \max(0, \min(1, F)).$$

6. Set the fluence equal to zero for all BEV pixels outside the projection of the PTV.

7. For each OAR, apply fluence reduction according the equation:

$$F = q_{OAR,j} F; q \in [0,1]; j \in \{1 \ldots N_{OAR}\}$$

where $N_{OAR}$ is the number of OARs. The equation is applied within the projection of OAR j, leaving regions outside the OAR unmodified, and $q_{OAR}$ is a fluence parameter that is specified for a particular beam and OAR.

Steps 1 through 7 are applied for each beam. Thus a modulated fluence pattern is calculated for each beam orientation. An advantage of this approach is that it automatically results in smooth fluence gradients over the PTV, and steep gradients at OAR boundaries, while requiring a minimal number of free parameters.

Discrete Cosine Transform Fluence Method

This method of producing a smoothly varying intensity pattern uses a few low-frequency terms of a two-dimensional Discrete Cosine Transform (DCT), where the terms are controlled by Ferret. The two-dimensional inverse DCT is appropriate (as opposed to a discrete Fourier transform) since it uses real-valued frequency components to produce a real-valued image:

$$f(x,y) = \sum_{u=0}^{N-1} \sum_{v=0}^{N-1} \alpha(u)\alpha(v) C(u,v) \cos\left[\frac{(2x+1)u\pi}{2N}\right] \cos\left[\frac{(2y+1)v\pi}{2N}\right]$$

$$\alpha(u) = \begin{cases} \sqrt{\dfrac{1}{N}} & u = 0 \\ \sqrt{\dfrac{2}{N}} & u = 1, 2, \ldots, N-1 \end{cases}$$

Here $C(u,v)$ is a frequency map of N pixels where the non-zero components (controlled by Ferret) are defined inside a sector with origin at the top left and a small radius. The radius of the sector may be increased to add higher frequency components for a more complex run.

The fluence for each beam is represented by a set of low frequency coefficients of a 2-dimensional DCT according to the following procedure:

1. Define the DCT plane as a 2-dimensional grid of pixels equal in size to the BEV plane, indexing DCT plane pixels according to i={1 ... Nx} and j={1 ... Ny}. Set all pixels on the DCT plane to equal zero.
2. Specify a small integer radius $r_{freq}$ and define an active DCT region as the set of pixels on the DCT plane where $i^2+j^2 \leq r_{freq}$.
3. Allow the Ferret Genetic Algorithm to directly control the values of pixels in the DCT active region.
4. Calculate a fluence pattern by performing a 2-dimensional inverse discrete cosine transform of the DCT plane.
5. Perform an upper and lower truncation of the resultant fluence pattern:

$F=\max(0,\min(1,F))$.

6. Set the fluence equal to zero for all BEV pixels outside the projection of the PTV.
7. For each OAR, apply a fluence reduction according the equation:

$F=q_{OAR,j}F; q\epsilon[0,1]; j\epsilon\{1 \ldots N_{OAR}\}$

Steps 1 through 7 are applied for each beam. Thus a modulated fluence pattern is calculated for each beam orientation. An advantage of this approach is that it automatically results in smooth fluence gradients over the PTV and steep gradients at OAR boundaries, while also limiting the number of free parameters that are required. The DCT fluence method is capable of a flexible degree of modulation that depends on $r_{freq}$, where larger values of $r_{freq}$ result in greater modulation.

It is possible to start a PARETO run using only a small number of DCT coefficients and add coefficients to increase fluence modulation as the run progresses. This is accomplished by increasing $r_{freq}$ at specified intervals during the optimization run. This method increases the number of parameters dynamically during the run, which takes advantage of functionality built in to Ferret that is designed for such applications.

Beam Group Fluence Method

Each beam is divided into a square grid of "pencil beam groups", and Ferret optimizes the normalized intensity value of the central beamlet within each group. Typical grid sizes are on the order of 5×5 to 10×10. Therefore, the parameters controlling representing the intensity of beam groups control a much larger number of beamlet intensities over the fluence pattern. The intensity of the non-central pencil beams within each group is calculated by two-dimensional interpolation over the beam groups. Fluence pixels that do not intersect with the PTV are assigned a value of zero, which creates a sharp edge at the PTV boundary.

The fluence for each beam is represented by dividing the BEV plane into a coarse N×M grid where each grid cell is defined as a beam group $B_{n,m}|n\epsilon\{1 \ldots N\}$ and $m\epsilon\{1 \ldots N\}$ and such that the entire BEV plane is covered by beam groups. The set of beam groups $\{B_{n,m}\}$ define the fluence pattern by the following procedure:

1. The value of each beam group is bounded such that $B_{n,m}\epsilon[0,1]$, where each $B_{n,m}$ is controlled directly by the Ferret Genetic Algorithm as an optimization parameter.
2. The values of pixels of the BEV plane are calculated by two-dimensional interpolation from the grid of beam groups.
3. Set the fluence equal to zero for all BEV pixels outside the projection of the PTV.
4. For each OAR, apply a fluence reduction according the equation:

$F=q_{OAR,j}F; q\epsilon[0,1]; j\epsilon\{1 \ldots N_{OAR}\}$

Steps 1 through 4 are applied for each beam, resulting in a modulated fluence pattern for each beam. An advantage of this approach is that it can result in highly modulated fluence patterns over the PTV, and steep gradients at OAR boundaries. However, the beam group approach usually requires more parameters than our other methods.

It is possible to adaptively refine the beam group grid, such that the number of beam group parameters increases as the run progresses. This procedure makes use of a special feature built in to Ferret, which allows the number of optimization parameters to vary during a run. This technique accelerates the run by allowing a coarse approximation to the optimal fluence pattern to be discovered early during the run, simultaneously with optimal beam angles. The latter part of the run would then focus on optimizing the fluence patterns more finely, as the beam group grid is made finer and beam angles are refined. This method offers the potential for very fine local control over fluence patterns.

Isodose Fluence Method

This parameterization is based on isodose-shaped aperture optimization. In our implementation, we first obtain a dose distribution from a certain set of beam angles using no fluence modulation other than OAR reduction parameters (see section 4 below). The shape of each field is determined by a margin parameter, which erodes or dilates the projection of the PTV in the BEV, as controlled by Ferret. From this basic dose distribution, we obtain a histogram of the PTV dose, and select the dose levels of the P strongest peaks, where P is approximately equal to seven, such that the number of peaks chosen corresponds to the number of fluence parameters selected for the run. Three-dimensional isodose surfaces are calculated at these dose levels and projected onto each BEV. For each BEV, the distinct pixel values arising from the sum of the projection masks are assigned weights controlled by Ferret. These final fluence maps are used to modulate the intensity of the rays already traced through the treatment volume. This method has the advantage of using the inherent non-uniformity of the target due to a solution's particular beam orientations and OAR reduction parameters to define important regions on the fluence map which may require a "boost" of radiation dose.

4. Applications of PARETO to Radiosurgery:

Stereotactic radiosurgery (SRS) is a specialty treatment within the broader context of radiation treatment, requiring higher doses and higher spatial accuracy of the radiation delivery. SRS treats a wide variety of disease sites, which present complex anatomical configurations that must be handled effectively during the radiation treatment planning process. PARETO improves the quality of SRS by (1) providing treatment plans superior to those provided by the standard commercial software, and (2) improving the overall efficiency of the treatment planning process for clinicians.

The SRS extension of PARETO includes the possibility of multiple targets and non-coplanar arcs and beam directions.

5. Applications of PARETO to Arc Therapy:

Volumetric Modulated Arc Therapy (VMAT) represents the state-of-the-art in radiation therapy because of its ability to deliver highly conformal dose distributions in a time efficient manner through a single 360 degree gantry arc. PARETO will optimize dose rate and multi-leaf collimator (MLC) positions during VMAT delivery to populate the trade-off surfaces of Pareto-optimal solutions. Coplanar and non-coplanar arcs will be modeled through a progressive sampling of static gantry and couch positions subject to the MLC translation speed and gantry/couch rotation speed constraints required for VMAT delivery. PARETO will optimize arc fluences, to achieve intensity modulation, through the progressive sampling of MLC positions.

Non-coplanar arcs will be treated as a three-dimensional parametric spatial curve, where Ferret optimizes the parameters describing the arc, while also optimizing the aperture shape at a fine sampling of positions along the arc.

6. Dose Calculation Description

Patient dose within PARETO is calculated via the standard 'convolution' method, where a point-dose kernel is convolved with a three dimensional map of total radiation energy released per unit mass (TERMA) which is proportional to fluence. A physics-based, two-source model calculates radiation fluence incident on the patient surface. This fluence model is based on the work of Chytyk and McCurdy (Med. Phys., 36(4):1389-98, 2009), but tailored for patient dose calculation. The point-dose kernel is generated based on the analytic fits to Monte Carlo data in the work of Ahnesjo (Med. Phys., 16(4):577-92, 1989). The TERMA calculation accounts for exponential attenuation and inverse-square effects. The convolution of the TERMA with the point-dose kernel mimics the effect of scattered radiation within the patient. It provides a reasonably accurate dose calculation in many situations, but any dose calculation method can be employed with PARETO. For example, more accurate algorithms such as the "collapsed cone superposition" method or the Monte Carlo method could in principle be used. However, the 'convolution' method or equivalent is a common option found in many commercial planning systems.

Within PARETO, we can use an accurate model of incident fluence (the two-source model mentioned above), or a less accurate but faster single source model.

7. Fitness Functions:

PARETO's multi-objective optimization requires a fitness function for the PTV and one for each OAR. Several alternative fitness functions for the PTV and OARs are built into the software. This section discusses alternative formulations and provides the detailed equations used by PARETO.

7.1. F-OAR-SIMPLE-VOLUMETRIC:

This is a simple OAR fitness function for volumetric structures, which is defined by the following equation:

$$F_{OAR,VOL} = \frac{N_{OAR,i}^{-1} \sum_{j=1}^{N} D_{OAR,i}}{M^{-1} \sum_{j=1}^{M} D_{PTV,i}}$$

This equation represents the mean OAR dose, normalized to mean PTV dose. $D_{PTV,j}$ is the dose applied to voxel j within the PTV, and $D_{OAR,i}$ is the dose applied to voxel i within an OAR. N and M are the number of OAR and PTV voxels respectively. The average PTV dose is identified with the prescribed dose to the target; thus $F_{OAR}$ represents the radiation exposure to an OAR in units of the prescribed dose. This normalization is advantageous because it allows us to work with dimensionless quantities and rescale our solutions, even after a run, to reflect adjustments to the prescribed dose, noting that any such rescaling of a Pareto non-dominated solution remains non-dominated. This formulation is most appropriate for volumetric OARs such as lungs. We have found the F-OAR-SIMPLE-VOLUMETRIC fitness function to be inferior to the F-OAR-DVH and F-OAR-EUD fitness functions discussed below in all tests.

7.2. F-OAR-SIMPLE-SERIAL:

This is a simple OAR fitness function for serial structures, which is defined by the following equation:

$$F_{OAR,SER} = \frac{\max(D_{OAR})}{M^{-1} \sum_{i=1}^{M} D_{PTV,i}}$$

This fitness function represents the maximum OAR dose, normalized to mean PTV dose. $D_{PTV,i}$ is the dose applied to voxel i within the PTV, and $\max(D_{OAR})$ is the maximum dose applied to the OAR. M is the number of PTV voxels. The average PTV dose is identified with the prescribed dose to the target; thus $F_{OAR}$ represents the maximum radiation exposure to an OAR in units of the prescribed dose. This formulation is most appropriate for serial OARs such as the spinal cord. We have found the F-OAR-SIMPLE-SERIAL fitness function to be inferior to the F-OAR-DVH and F-OAR-EUD fitness functions in all PARETO tests.

7.3. F-OAR-DVH:

This OAR fitness function is based on the evaluation of dose volume histograms. The F-OAR-DVH fitness function is defined by the following equations:

$$F_{OAR} = \frac{1}{V_{OAR}} \left[ \sum_{i=1}^{N} f_i^p \Delta V_{OAR,i} \right]^{1/p} ; f_i \equiv \left\{ \begin{array}{ll} 0, & D_i \leq D_0 \\ D_i/D_0, & D_i > D_0 \end{array} \right\}$$

This fitness function represents the volume-weighted mean thresholded dose computed from a dose-volume histogram (DVH) with N bins. $\Delta V_{OAR,i}$ is the increment in volume from the i'th bin of the DVH curve and $V_{OAR}$ is the total volume. $D_i$ is dose and $D_0$ is the target dose threshold for the OAR, Voxels receiving the highest dose are more strongly suppressed for larger values of exponent $p \geq 1$. Values of p=1 is appropriate for volumetric structures, while p>1 is appropriate for serial structures. This fitness function most closely mimics the decision making process used clinically. It is known to outperform the F-OAR-SIMPLE fitness functions in all PARETO tests, and is comparable to the F-OAR-EUD fitness function defined below.

7.4. F-OAR-EUD:

This OAR fitness function is based on the biological principle of equivalent uniform dose. The F-OAR-EUD fitness function is defined by the following equation:

$$F_{EUD} = \left( \sum_{i=1}^{N} f_i^p \right)^{1/p} ; f_i \equiv \left\{ \begin{array}{ll} 0, & D_i \leq D_0 \\ D_i/D_0, & D_i > D_0 \end{array} \right\}$$

This equation represents the equivalent uniform dose with dose threshold $D_0$. $D_i$ is dose at voxel i and $D_0$ is the target dose threshold for the OAR. N is the number of OAR and PTV voxels, respectively. Exponent p=1 best corresponds to volumetric structures, while values of p>1 are most appropriate for serial structures. We have determined that this fitness function is superior to the F-OAR-SIMPLE fitness functions in all PARETO tests, and competitive with the F-OAR-DVH fitness function.

7.5. F-PTV-STD:

This PTV fitness function is based on minimizing the standard deviation of the dose over voxels within the PTV. The F-PTV-STD function is defined by the equation:

$$F_{PTV} = \frac{\left[\sum_{i=1}^{M}(D_{PTV,i} - \overline{D})^2\right]^{\frac{1}{2}}}{\sum_{i=1}^{M} D_{PTV,i}}$$

where $D_{PTV,i}$ is dose at voxel i within the PTV, $\overline{D}$ is the average dose over the PTV, and M is the number of voxels in the PTV. This fitness function may result in a more uniform dose over the PTV than the F-PTV-CONF function defined below, but it has the major drawback that it does not suppress dose exterior to the PTV. Moreover, it is not compatible with the hotspot suppression penalty functions discussed below.

7.6. F-PTV-CONF:

This PTV fitness function is designed to optimize the conformity of the radiation dose to the PTV. This conformity fitness function is based on the statistical correlation function between a dose proxy matrix D and a planning-target-volume mask M, where M is defined such that a value of 1 is assigned to all voxels inside the PTV and 0 outside, and is defined according to the equations:

$$F_{PTV} = \log_{10}\left\{\frac{1}{2}\left[1 - \frac{\sum_{i=1}^{N} Q_i(D_i - \overline{D})(M_i - \overline{M})}{\sigma_D \sigma_M}\right]\right\}$$

$$\sigma_D = \left(\frac{\sum_{i=1}^{N} Q_i(D_i - \overline{D})^2}{\sum_{i=1}^{N} Q_i}\right)^{\frac{1}{2}} \quad \sigma_M = \left(\frac{\sum_{i=1}^{N} Q_i(M_i - \overline{M})^2}{\sum_{i=1}^{N} Q_i}\right)^{\frac{1}{2}}$$

where $\sigma_D$ and $\sigma_M$ are the weighted dose and mask standard deviations, respectively, and N is the total number of voxels inside the patient volume. Weight matrix $Q_i$ specifies the weight applied to voxel i, and therefore determines the relative weight applied interior and exterior to the PTV. Generally, we apply more weight to the PTV than to surrounding voxels. The F-PTV-CONF fitness function is regarded as superior to the F-PTV-STD function due to its ability to suppress dose external to the PTV, thus emphasizing sharp boundaries between the PTV and other healthy tissue.

7.7. F-PTV-CONF-HOTZONE:

A variation of the F-PTV-CONF defines a "hot zone" consisting of voxels near the PTV, where $d_i$ is the distance from voxel i such that $d_i \leq f_{PTV}*d_{PTV}$, where $d_i$ is the distance within the treatment volume to the nearest voxel within the PTV structure, and $d_{PTV}$ is the maximum distance between voxels within the PTV. The fraction $f_{PTV}$ therefore represents the linear extent of the hot zone relative to the maximum linear size of the PTV. We normally set $f_{PTV} \leq 0.5$. In this variation of F-PTV-CONF, $Q_i=0$ within the cool zone, such that the conformity function is applied only to voxels within the PTV and the hot zone. This fitness function should normally be used with one of the suppression penalty functions discussed below (although this is not strictly required), where $f_{PTV}$ is defined consistently. We find that the hot zone-limited conformity function results in better conformity near the PTV, while the hotspot suppression penalty function eliminates hotspots in the "cool zone" exterior to the hot zone.

7.8. Hotspot Suppression Penalty Function #1:

None of the OAR fitness functions discussed above penalize regions of high dose in other healthy tissue (OHT) outside of OARs. The PTV conformity fitness function F-PTV-CONF decreases hotspots, but less effectively than desired. We have therefore developed a function defined by the following equation, which strongly penalizes hotspots in OHT distant from the PTV:

$$F_{penalty} = \begin{cases} F_0 * \left(1 + \max\left\{\frac{d_i}{d_0}\right\}\right) & \text{if } \exists \text{ voxels } i \mid d_i > f_{PTV} * d_{PTV} \text{ and } D_i > D_{OHT}; i \in \{1 \ldots N\} \\ 0 & \text{otherwise} \end{cases}$$

where $d_1$ is the distance from voxel i within the treatment volume to the nearest voxel within the PTV structure, and $d_0$ is the maximum value of $d_i$ over all N voxels within the treatment volume exterior to the PTV. $F_0$ is a number that represent the typical scale of the penalty, which is chosen to be greater than typical values of all other fitness functions; for example, $F_0=10$ is a common choice. $F_{penalty}$ is added to all other fitness functions.

The size of the "hot zone" near the PTV is given by the product $f_{PTV}*d_{PTV}$, where $f_{PTV}$ is a fractional value (usually less than or equal to 0.5) representing the extent of the hot zone relative to the maximum PTV linear size $d_{PTV}$. Regions within the treatment volume and exterior to the hot zone ($d_i > f_{PTV}*d_{PTV}$) are referred to as the "cool zone". The radiation dose is necessarily high within the hot zone, due to the intersection of a large number of beams and the proximity to the PTV.

This penalty function is designed to penalize solutions that contain extensions of high radiation dose containing hot voxels in the cool zone, where a hot voxel is defined as one where the dose is greater than the allowable OHT dose $D_{OHT}$. For example, a penalty is applied, which increases linearly with the maximum distance to any hot voxel within the cool zone. The penalty function is equal to zero if there are no hot voxels within the cool zone. Thus, the fitness functions are unaffected once all hotspots have been eliminated. This hotspot suppression function works best in conjunction with the F-PTF-CONF-HOTZONE fitness function.

7.9. Hotspot Suppression Penalty Function #2:

We define a second penalty function by the equations:

$$\text{dose\_violation} = \max\left\{0, \left(\frac{D_i - D_{OHT}}{D_{OHT}}\right)\right\} \forall i \in \{1 \ldots N\} \mid d_i > f_{PTV} * d_{PTV}$$

$$F_{penalty} = \begin{cases} 0, & \text{if dose\_violation} = 0 \\ F_0 + \text{dose\_violation}, & \text{if dose\_violation} > 0 \end{cases}$$

where $d_i$ is the distance from voxel i within the treatment volume to the nearest voxel within the PTV structure, and $d_{PTV}$ represents the maximum distance between voxels within the PTV. The size of the "hot zone" near the PTV is given by the product $f_{PTV}*d_{PTV}$, where $f_{PTV}$ is a fractional value usually less than or equal to 0.5. $F_0$ is the typical scale of the penalty, which is chosen to be greater than typical values of all other fitness functions; for example, $F_0=10$ is a common choice. $F_{penalty}$ is added to all other fitness functions. Regions within the treatment volume and exterior to the hot zone ($d_i>f_{PTV}*d_{PTV}$) are referred to as the "cool zone". The radiation dose is necessarily high within the hot zone, due to the intersection of a large number of beams and the proximity to the PTV.

This penalty function is designed to penalize solutions that contain hot voxels within the cool zone, where a hot voxel is defined as one where the dose is greater than the allowable OHT dose $D_{OHT}$. For example, a penalty is applied, which increases linearly with the fractional degree by which the allowable OHT dose is exceeded. The penalty function is equal to zero if there are no hot voxels within the cool zone. Thus, the fitness functions are unaffected once all hotspots have been eliminated. This hotspot suppression function works best with the F-PTF-CONF-HOTZONE fitness function.

It has not been determined which hotspot suppression penalty function offers superior hotspot suppression. However, we prefer Hotspot Suppression Penalty Function #2 because of its simpler implementation.

7.10. Rapid Distance Calculation Using Fast Fourier Transforms:

The F-PTV-CONF-HOTSPOT fitness function and both hotspot suppression penalty functions require the distance from all voxels within the treatment volume exterior to the PTV to the nearest voxel within the PTV. The exact calculation of these distance elements is a computationally intensive process. Therefore, we have developed a rapid method based on Fourier transforms that is sufficiently accurate for use in our F-PTV-CONF-HOTSPOT fitness function and hotspot suppression penalty functions. The algorithm is defined by the following sequence of steps:
1. Define n to be an integer greater than approximately 25.
2. Define a matrix R containing radius values such that $R=[(X-x_0)^2+(Y-y_0)^2+(Z-y_0)^2]^{1/2}$ where X, Y, and Z are matrices of Cartesian coordinate values for the voxels constructed from coordinate vectors x, y, and z; and $x_0$, $y_0$, and $z_0$ are the coordinates of a central voxel such that $x_0=x(floor((Nx/2)+1))$, $y_0=x(floor((Ny/2)+1))$, and $z_0=z(floor((Nz/2)+1))$, where Nx, Ny, and Ny are the lengths of coordinate vectors x, y, and z respectively.
3. Redefine values of R equal to zero to be equal to the smallest non-zero value of R.
4. Calculate a matrix of approximate distances $d=\{d_i\}$ by performing the convolution: $d=[conv(M, R^{-n})]^{-1/n}$.

This method works because $R^{-n}$ is a function that falls rapidly with distance R. Thus, the convolution with mask array M is dominated by the nearest non-zero element within the mask. It is simple to verify the algorithm for the special case where M contains only a single non-zero voxel centred on a voxel at position $(x_0,y_0,z_0)$. In this case, $conv(M, R^{-n}) \approx [(x-x_0)^2+(y-y_0)^2+(z-z_0)^2]^{n/2}$, so that d is an accurate representation of the distance. The advantage of this method over direct calculation is due to the high speed and efficiency of FFT calculations.

7.12. Beam Number Optimization:

PARETO can be run in a mode that allows beams to merge when their angular separation on a sphere defined by $(\theta, \phi)$ is less than a threshold value, which is typically 10 to 15 degrees. PARETO performs a recursive binary search that identifies and merges beams closer than this threshold angle, in order of increasing angular separation, and stops when no two beams are closer than the threshold. A beam merger averages the vector position of two beams on the unit sphere and also averages their fluence parameters prior to the evaluation of the fitness function. Merging results in two identical beams. However, PARETO ignores duplicate beams by sending only one copy of the merged pair to the ray tracer and fitness functions.

Beam merging is performed for a solution according the following procedure:
1. The user selects a minimum beam angle $\Delta\alpha_0$ for beam merging, such that beams closer in angle than $\Delta\alpha_0$ will be merged.
2. The angular distance is calculated between all beam pairs on a unit sphere according to the procedure:
   a. Each beam orientation $(\theta, \phi)$ is converted to Cartesian coordinates $x=(x,y,z)$ on the unit sphere.
   b. The angle $\Delta\alpha$ between each beam pair in degrees is calculated according to the formula:

$$\Delta\alpha(x_1, x_2) = \frac{180}{\pi}\cos^{-1}\left(\frac{x_1 \cdot x_2}{\|x_1\|\|x_2\|}\right).$$

3. An array A is generated where the entry in row i and column j is either NaN if $\Delta\alpha(x_i,x_j)>\Delta\alpha_0$, or equal to $\Delta\alpha(x_i,x_j)$ if $\Delta\alpha(x_i,x_j)<=\Delta\alpha_0$.
4. If $\Delta\alpha(x_i,x_j)=0$, then set $\Delta\alpha(x_i,x_j)=NaN$.
5. The following steps are performed in a loop while matrix A contains finite elements (not NaN):
   a. The smallest finite (not NaN) entry in A is selected for merging and beams with beam numbers corresponding to row i and column j of matrix A are merged according to the procedure:
      i. The beam angle parameters and fluence parameters for the two beams are averaged
      ii. Both beams are replaced with a copy of the merged beam.
   b. Array A is updated following steps 2 to 4.
6. The merging procedure exits when all elements of array A are NaN.

Thus, beam angles are merged recursively until no pair of beams remains with angular separation less than $\Delta\alpha_0$. If two or more beams contain identical orientations, then only the first identical beam is used to calculate radiation dose; the other identical beams are effectively turned off since they are not used for ray tracing or dose calculation.

It is a subtle point that beam angles modified by merging are evaluated 'on the fly' by the fitness function, but are not re-inserted back into the GA population via the parameter re-insertion mechanism used for beam sorting. Merging beams results in the duplication of parameters, which would severely degrade the diversity of parameter values present in the genetic algorithm population and damage the search if re-insertion were allowed. Note that beam merging is fundamentally different from beam sorting, which does not result in parameter duplication and helps the search by decreasing the size of the parameter space.

A result of beam merging is that the genetic algorithm population is comprised of solutions requiring differing numbers of beams. PARETO minimizes the number of beams as a secondary objective to the PTV and OAR fitness functions. This beam number minimization is accomplished by adding a small penalty function $\Delta F=10^{-6}N_{beams}$ to all fitness functions to slightly prefer solutions with fewer beams, where $N_{beams}$ is the number of unique beams. (Recall that Ferret is a minimizer.)

8. Customized Ray Tracing

An efficient ray tracer/caster is essential to being able to produce results in an acceptable time. A ray tracer/caster is a computer code required to calculate radiological path-length and therefore modify radiation fluences as they pass through the patient model. PARETO's ray tracer/caster has features that allow it to efficiently ray trace/cast through a three-dimensional matrix of the size of the phantom/patient data know as the treatment volume. This efficiency is accomplished due to the following features:

1. Only casting a ray through the treatment volume if it would pass through a pixel on a 2D projection known as a Beams Eye View (BEV), of the Planning Treatment Volume (PTV), which represents the target to be irradiated.
2. Calculating the entrance and exit points of the ray through the treatment volume in order to calculate the number of steps to take for a ray before casting.
3. Using a non-standard and very efficient approximation of the exponential function to calculate fluence attenuation, as discussed below.
4. Fluence is only calculated when the ray travels within the patient structure (i.e. 'skin').
5. A list that relates each BEV pixel to corresponding voxels in the treatment volume where fluence/intensity values is recorded. This provides flexibility in implementation such that rays can be modified in accordance with BEV values after the ray trace/cast, if they were not modified beforehand.

Ray Tracing/Casting Algorithm

The ray-tracing/casting algorithm is defined by the following procedure:

1) PTV 3D contour data is rotated by a given (gantry, couch) angle set and projected onto a 2D plane to compute the BEV.
2) A fluence method defined a priori can be applied to the BEV.
3) BEV, gantry/couch angles, treatment geometry, patient density model, and table of attenuation coefficients are passed to the ray tracer.
   a) Source point of the treatment device is rotated by (gantry, couch) angle to match BEV.
   b) BEV is scanned over until a non-zero pixel is located. The value of the non zero pixel becomes the initial intensity of the ray.
   c) An intersection between a line and a plane representing the faces of the treatment volume is found. This represents the entrance location in the cube.
   d) Using the same line, an intersection between the line and the treatment volume is found again representing the exit location.
   e) The number of steps for the ray is calculated.
   f) For each step, check if the current voxel coincides with a voxel within the skin:
      i) if it coincides:
         (1) Look up voxel location in attenuation coefficient matrix
         (2) Calculate attenuation of fluence to the voxel of interest according to the equation:

$$\phi=\phi_0 \cdot \exp(-\mu_{voxel_i} \cdot l)$$

where $\phi_0$ is the initial fluence entering the patient, obtained from the BEV, $\mu_{voxel_i}$ is obtained from a linear attenuation coefficient matrix at same $voxel_i$, and l is the radiological path length $voxel_i$ as determined by the ray tracer/caster (3) record information at voxel location in treatment volume from above equation, and record voxel location in separate list which relates BEV pixel to voxel location in treatment volume.
      ii) if not: Record no information in treatment volume or BEV pixel to voxel location list.
   g) Terminate the ray tracer/caster after all non zero BEV pixels have been traced/casted.
4) If fluence was not applied to the BEV in step 2, a fluence method may be applied to the BEV and using the BEV pixel to voxel location list be applied to the traced/casted rays.
5) A three-dimensional scatter kernel (representing the radiation dose spread pattern outwards from an ideal point of interaction in the patient volume) is rotated by (gantry, couch) angle set.
6) The fluence pattern in the patient calculated using the traced/casted rays are then convolved with the scatter kernel created in step 5.

Method for Fast Calculation of the Exponential Function:

In order to calculate how the fluence intensity changes (exponential equation in the previous section) along the path of a single ray, the exponential function must be called a large number of times. Standard math libraries include an exponential function that is very accurate but also slow. Some math libraries include a faster but less accurate approximate exponential function using a look up table with interpolation methods.

The method used in PARETO is a new application of a technique that was originally designed for applications in neural network simulations (N. N. Schraudolph, "A fast, compact approximation of the exponential function," *Neural Computation*, 1999). The method involves manipulating the IEEE floating point representation and has been shown to give comparable approximation results.

To do this floating point numbers are represented in IEEE-754 by the equation $$(-1)^s 2^{exponent-exponentbias}(1.m)$$

where for double precision s is the sign bit representing negative and positive numbers, exponent is 11 bits with the bias of 1023 and in the mantissa or significance of 52 explicitly stored bits which contains the significant digits. Components may be accessed through the same memory location as a pair of 4 byte integers, so an integer written to the exponent location in memory will be read back exponentiated from the floating point format. This method has the slight drawback that since it accesses bytes of memory the ordering of the bytes is important and care must be taken to ensure that it is set up in the correct way per system. If the exponent is located in the higher order bits then for an integer x to compute $2^x$ it must be left-shifted by 20 bits, so $i=2^{20}(x+1023)$. For non-integer values of x, after multiplication the non-integer elements will be carried over to the higher bits of the mantissa. This, by the IEEE-754 standard, produces a nearest neighbor interpolation on the nearest two exponent values, and hence becomes faster than a normal interpolated lookup table:

$$i = \frac{2^{20}x + (1023 \cdot 2^{20} - c)}{\ln 2}$$

where c is a adjustment parameter that can give control over the approximation.

9. Use of Graphical Processing Units (GPUs) for Speed Increases

In order to increase the speed of calculation, PARETO contains an option to use nVidia graphics processing unit(s) (GPUs) together with nVidia's Compute Unified Device Architecture (CUDA) language for certain mathematical operations. Using the GPU and CUDA gives the advantage of a large parallel computing architecture from an off-the-shelf GPU, for example an nVidia GeForce GTX 480 (www.nvidia.com) has 480 CUDA processing cores each at a clock speed of 1400 MHz.

Profiling PARETO's CPU performance allowed bottlenecks to be found in order to write those routines in CUDA. This analysis has motivated us to rewrite the ray tracer/caster and Fast Fourier Transform (FFT) convolution into CUDA. nVidia provides a CUFFT library for doing FFT work, whereas the ray tracer/caster had to be written for CUDA.

PARETO's implementation uses a multiple-server queue method so that for a user with hardware that has N GPUs and N CPU cores, data is processed in an efficient manner. In order to avoid costly transfers of large data sets between the CPU and the GPU per data set evaluation, a global common set of data (convolution parameters, patient/phantom geometry) was stored in the GPU memory.

GPU Acceleration Procedure

The following definitions are used in this section:
1. Treatment volume: the three-dimensional array of voxels of size (M×N×P) representing the patient/phantom to be treated.
2. Patient/Phantom Geometry: (x,y,z) pixel sizes, output matrix size (M×N×P), source of radiation to planned treatment volume (PTV) centre distance, step length to take on each increment of a ray, binary skin mask of size of output matrix and patient/phantom attenuation matrix of size of output matrix.
3. Convolution Parameters: The size of the scatter kernel matrix.
4. Beams Eye View: A 2D projection of the planned treatment volume (PTV) from 3D contour data rotated by a (gantry, couch) angle set.

The GPU procedure is defined by the following steps:
1) Start N specified servers where 0≤N≤number of GPUs and CPU cores available
   a) Memory is shared for patient/phantom geometry, skin mask, convolution parameters, ray entrance/exits. Results are zeroed and unlocked for each GPU to be used.
2) Treatment geometry, skin mask, convolution parameters are passed to GPUs and validated (dimensions of skin mask, treatment volume, output matrix, attenuation matrix and convolution parameters are the same and present).
   a) Skin mask, treatment volume, and convolution parameters are checked to see if dimensions are a power of 2. If not, pad everything to same size power of 2.
3) A data set is de-queued and passed to an available GPU.
4) The scatter kernel is rotated by (gantry, couch) angle set and padded.
5) The BEV and (gantry, couch) angle set is passed to the ray tracer/caster.
6) On the CPU, the entrance and exit locations of each ray is found. This is done by scanning over the BEV and finding the intersection on the treatment volume of a line passing through the BEV for a non-zero pixel and treatment volume.
7) The information from 6 is passed to the GPU.
8) In parallel on the GPU all rays is traced/casted using information from 6.
   a) A check is performed if current voxel coincides with a skin mask voxel.
   b) If the current voxel coincides with a mask voxel within the skin, the attenuation coefficient is found for the same voxel in attenuation matrix. The attenuation value is used to calculate an inverse exponentially attenuated value and recorded in output matrix at specific voxel. Take another step along the path.
   c) If does not coincide, take another step
   d) Repeat until exit is reached (no more steps)
9) A FFT convolution of the result from 8d and the scatter kernel from 4 is performed on the GPU.
10) The result from 9 is passed back from the GPU to CPU (host) memory.
11) Continue from 3 until queue is empty.

10. Examples of PARETO's Use on Test Problems

This section shows several illustrative examples of PARETO optimization runs for artificial data (phantoms) and real patient data.

10.1. A Simple Test Problem Using a Cylindrical Geometric Phantom

Figure 4:
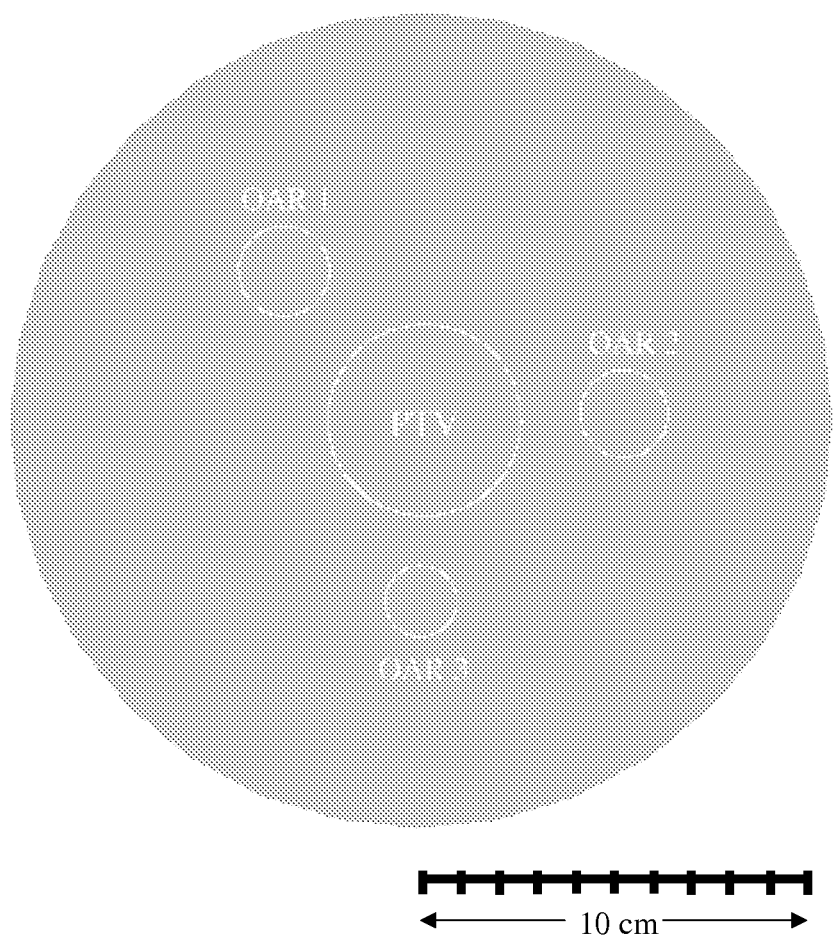
FIG. 4 is a representation of an axial slice of a simple artificial data set used to test PARETO, which is referred to as the cylindrical phantom.

FIG. 4 shows an axial slice of a homogeneous geometrical phantom used as a simple test problem for PARETO. The phantom is comprised of a cylindrical PTV surrounded by three OARs within a cylindrical skin structure with a radius of approximately 10 cm. The phantom is defined within a treatment volume of x-y-z dimension equal to 62×61×13 with the PTV and OAR structures residing on the central 7 slices in the z direction. The test allowed a maximum of 10 beams with PARETO's beam merging feature enabled.

Figure 6:
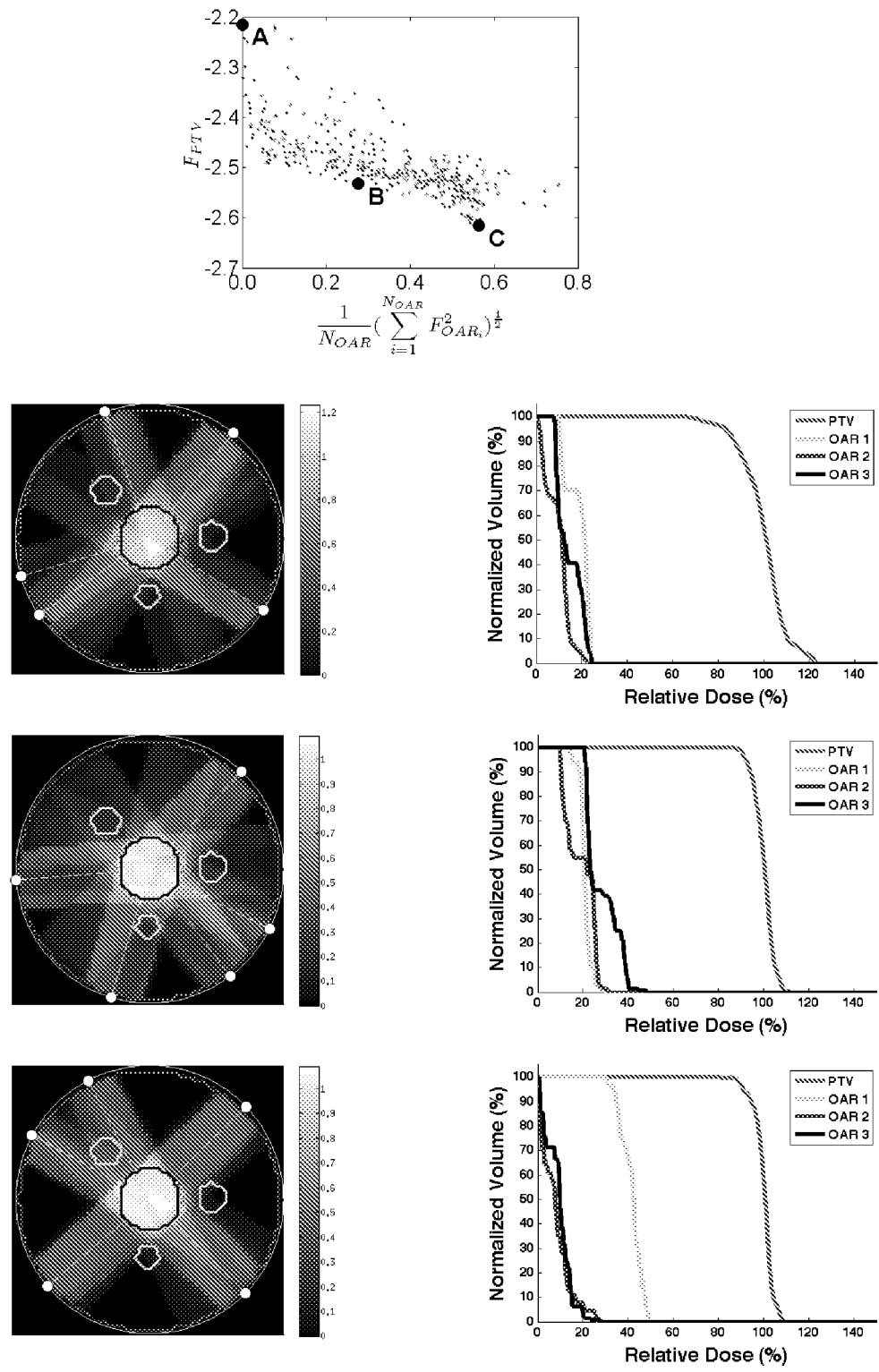
FIG. 6 is a representation of the Pareto non-dominated solution set obtained from a PARETO run using the cylindrical phantom with the F-PTV-CONF-HOTSPOT fitness function and the F-OAR-DVH (dose threshold=25%) fitness function, followed by images of the radiation dose patterns and DVH curves for three sample solutions.
Figure 7:
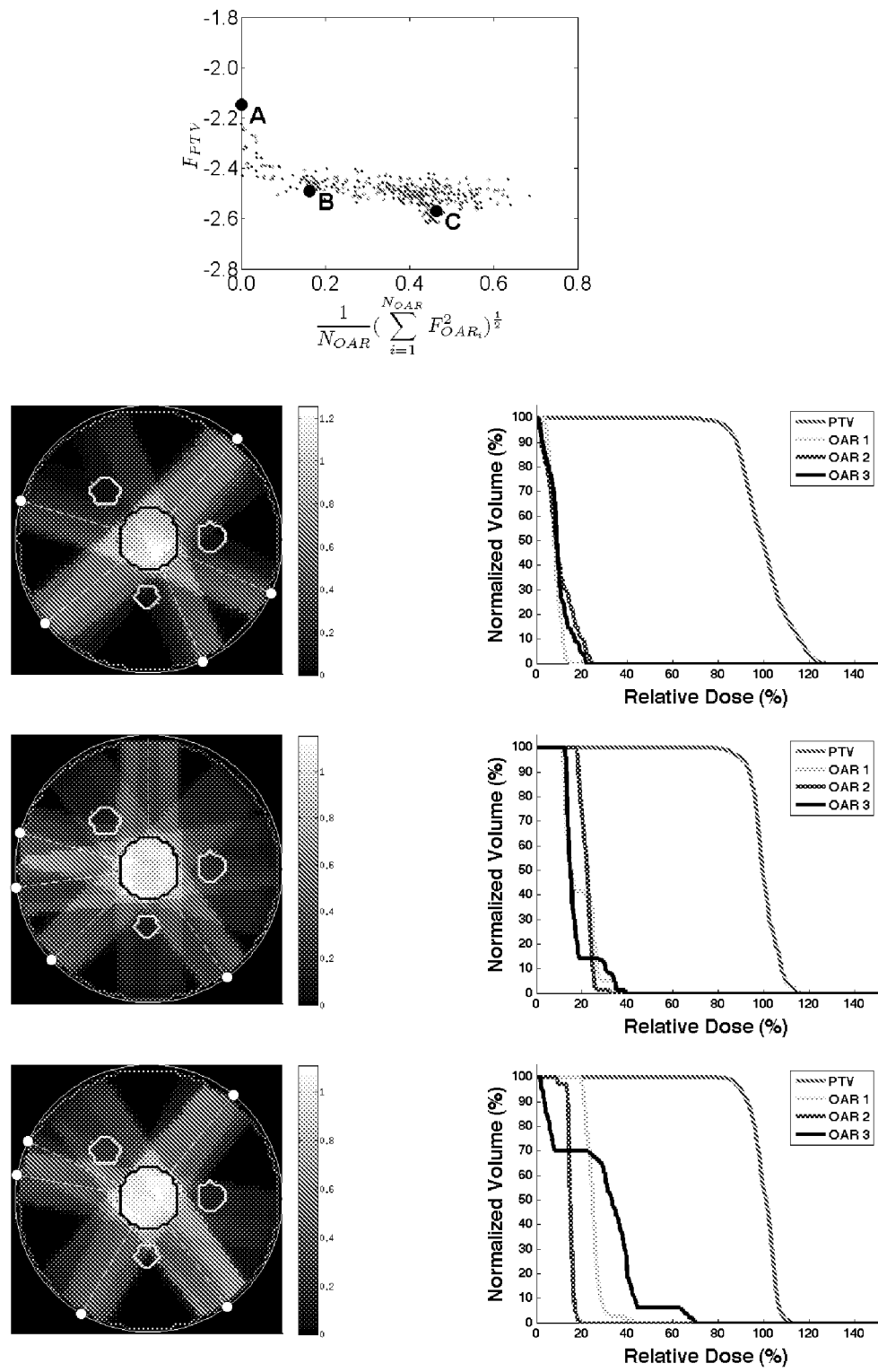
FIG. 7 is a representation of the Pareto non-dominated solution set obtained from a PARETO run using the cylindrical phantom with the F-PTV-CONF-HOTSPOT fitness function and the F-OAR-EUD (dose threshold=25%) fitness function, followed by images of the radiation dose patterns and DVH curves for three sample solutions.

We have tested PARETO on this phantom using the linear gradient fluence method. Ferret is a multi-population genetic algorithm, where multiple populations can run simultaneously, with minimal communication between populations. The run was set up using 3 populations of 100 individuals (trial solutions) and run for 1000 generations. FIG. 6 shows results using the F-PTV-CONF-HOTSPOT and F-OAR-DVH fitness functions. FIG. 7 shows results using the F-PTV-CONF-HOTSPOT and F-OAR-EUD fitness functions. Results from these runs are of similar high quality.

We have also separately tested the F-PTV-STD fitness function and the F-OAR-SIMPLE fitness function on the cylindrical phantom. These fitness functions perform poorly compared to our other fitness functions, and therefore results are not shown. The F-OAR-SIMPLE function places too much emphasis on reducing dose below normal clinical thresholds and very few balanced solutions were discovered using this function. Solution sets typically contained a few good solutions, but these were diluted by a large number of poor solutions characterized by extremely low dose for one or more OARs, but unacceptably high dose for other OARs and poor PTV uniformity. This problem is remedied by fitness functions that include a dose threshold $D_0$ for each OAR (F-OAR-DVH and F-OAR-EUD). The F-PTV-STD fitness function resulted in a poor spatial distribution of beams. With this PTV fitness function, PARETO typically reduced the effective number of beams by causing pairs of beams to overlap while decreasing the intensity of each. However, these solutions suffered from a serious defect characterized by poor conformity to the PTV. Severe hotspots of dose exterior to the PTV were not suppressed because the uniformity fitness function computed the standard deviation of the dose over the PTV only, without considering voxels outside.

Figure 8:
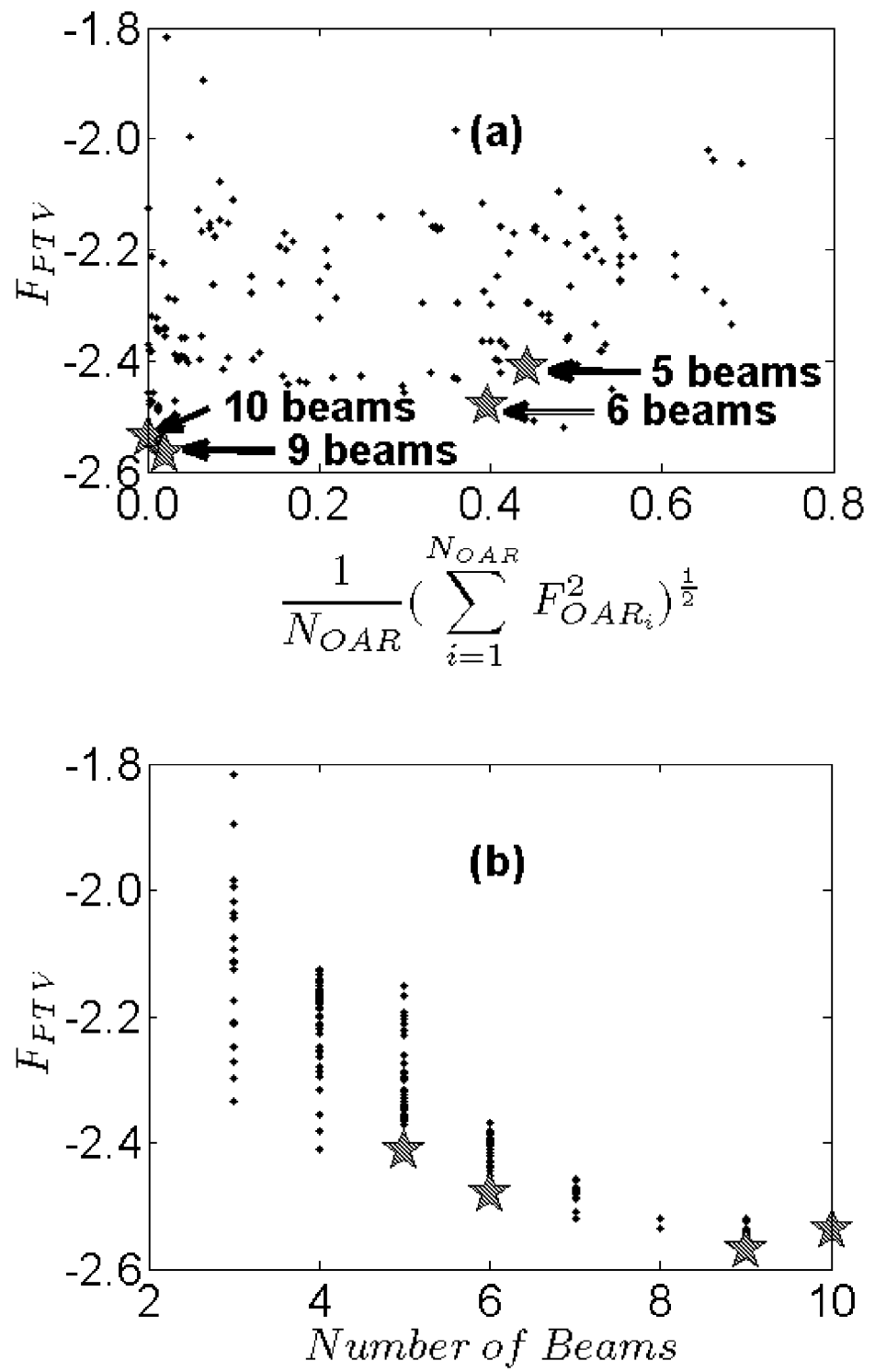
FIG. 8 is a representation of the Pareto non-dominated solution set obtained from a PARETO run using the cylindrical phantom with the F-PTV-CONF-HOTSPOT fitness function and the F-OAR-DVH (dose threshold=25%) fitness function with beam merging enabled, with specific solutions highlighted that require different numbers of beams, followed by a graph showing the variation of the F-PTV-CONF function with the number of beams required.

FIG. 8 shows the effect of optimizing the number of beams where beams closer than 15 degrees were merged. A slight perturbation $\Delta F=10^{-6}N_{beams}$ was added to all fitness functions to slightly prefer solutions with fewer beams, where $N_{beams}$ is the number of unique beams. The most conformal plan (with the lowest $F_{PTV}$) discovered made use of 9 beams. There is a general trend of improving conformity as the number of beams is increased, but this effect saturates at 9 beams. FIG. 8 shows DVH curves for the PTV and each OAR separately for the solutions highlighted in FIG. 7. We observe a general trend of improvement in the DVH curves as the number of beams is increased; the PTV DVH tends to become flatter (more uniform dose) with a sharper fall-off near 100% of the prescribed dose, while the OAR DVH curves tend to become narrower due to lower overall dose.

Figure 10:
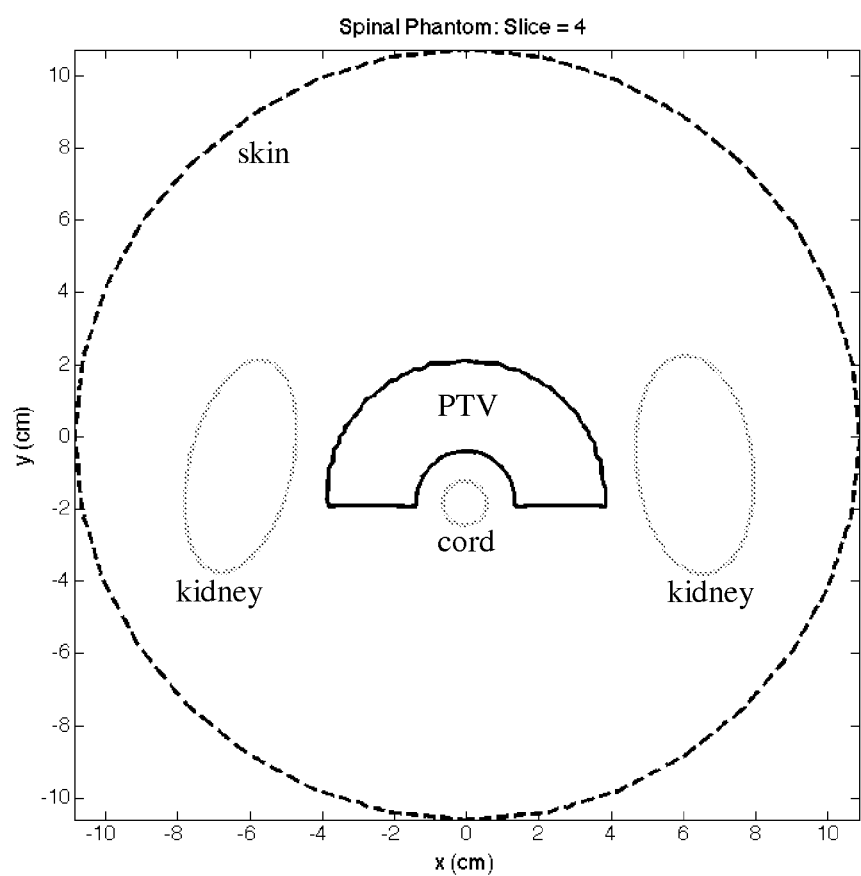
FIG. 10 is a representation of an axial slice of a challenging artificial data set used to test PARETO, which is referred to as the spinal phantom.

10.2. A Challenging Test Problem Using Spinal Phantom with a Homogeneous C-Shaped PTV Wrapped Around a Spinal Cord FIG. 10 shows a challenging phantom that includes a C-shaped PTV structure that is partially wrapped around an OAR representing a spinal cord. Two larger OARs representing the patient's kidneys surround the PTV. The phantom is defined within a treatment volume of x-y-z dimension equal to 62×61×13 with the PTV and OAR structures residing on the central 7 slices in the z direction.

Runs were set up using 3 populations of 100 individuals and run for 1000 generations using the Discrete Cosine Transform method for fluence modulation. The F-PTV-CONF-HOTSPOT fitness function was used in conjunction with the conformity fitness function F-OAR-DVH and hotspot penalty function #2. We used a maximum of 12 beams, with beam merging allowed.

Figure 11:
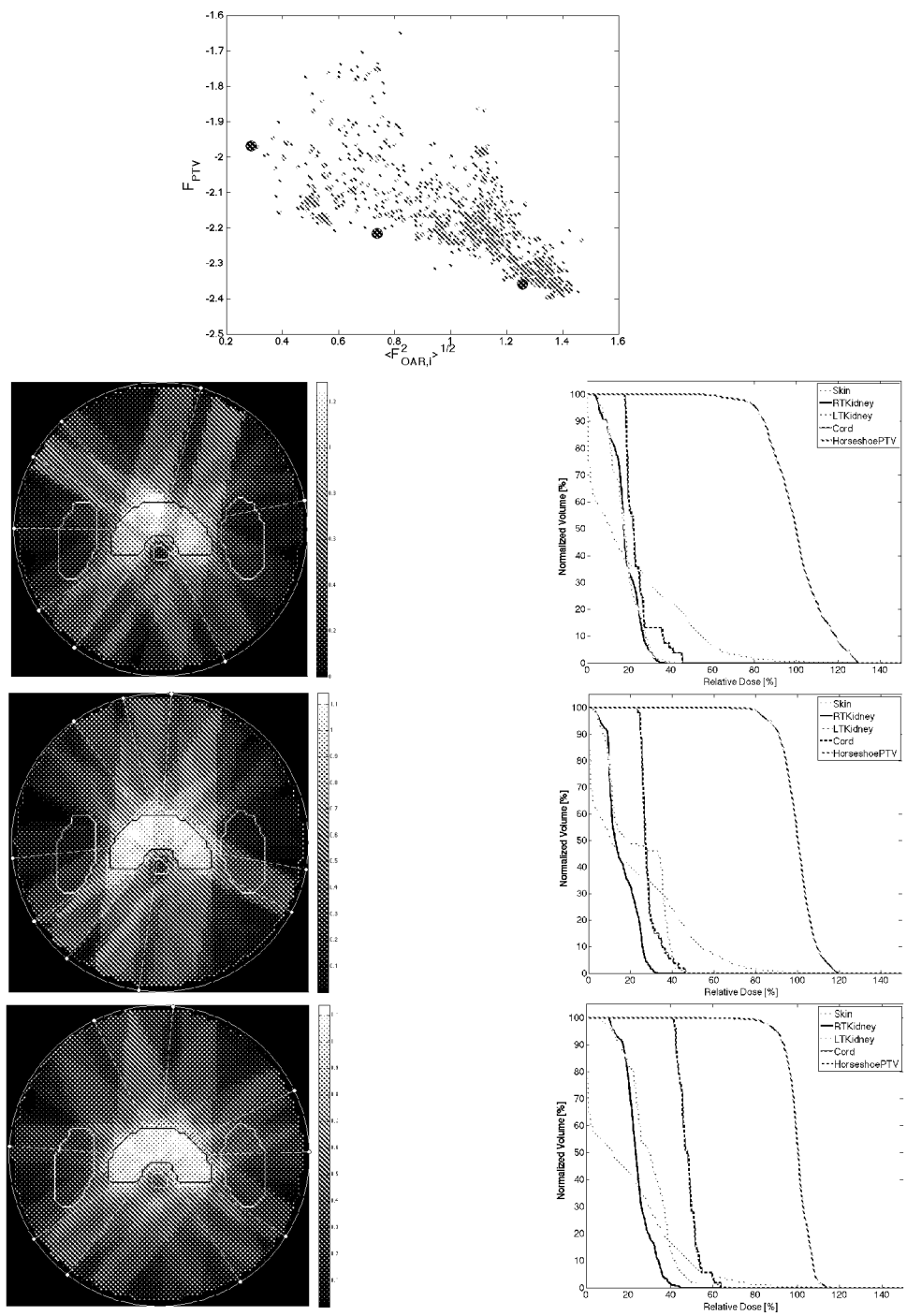
FIG. 11 is a representation of the Pareto non-dominated solution set obtained from a PARETO run using the spinal phantom with solutions evaluated using the PTV-CONF-HOTSPOT fitness function, the F-OAR-DVH (dose threshold=25%) fitness function, and hotspot suppression penalty function #2 with beam merging enabled, followed by images of the radiation dose patterns and DVH curves for three sample solutions.

FIG. 11 shows a projection of the trade-off surface, where the OAR fitness values have been averaged in quadrature for display purposes. The figure also shows axial projections of the radiation pattern and corresponding DVH curves for three different solutions that are shown on the trade-off surface. Solutions show a high degree of conformity to the PTV and the PTV DVH curve shows excellent dose uniformity, especially in solutions B and C, which emphasize PTV uniformity over OAR sparing. An increase in OAR dose is observed in the DVH curves as PTV conformity increases. No hotspots are present for any solutions contained within the Pareto non-dominated set.

Figure 12:
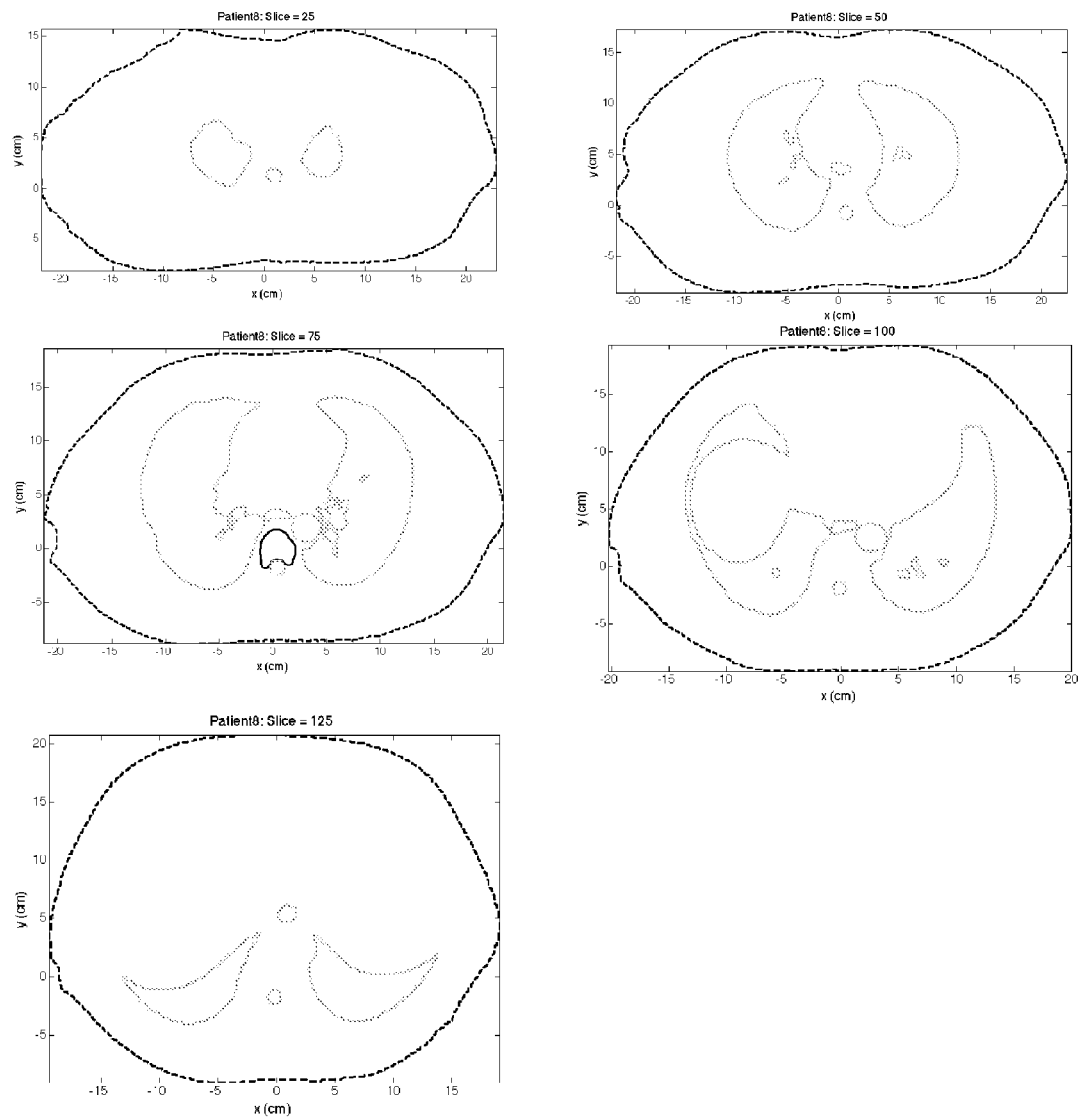
FIG. 12 is a representation of five axial slices selected from a patient data set showing contours of the PTV, OARs, and skin, where the data represented is referred to as the patient data set.

10.3. A Test Problem Using Patient Data with Homogeneous Attenuation Coefficient FIG. 12 shows a set of axial slices of the contours defining the PTV and the OARs for a real patient data set. This complex geometry provides a realistic test of PARETO.

Figure 13:
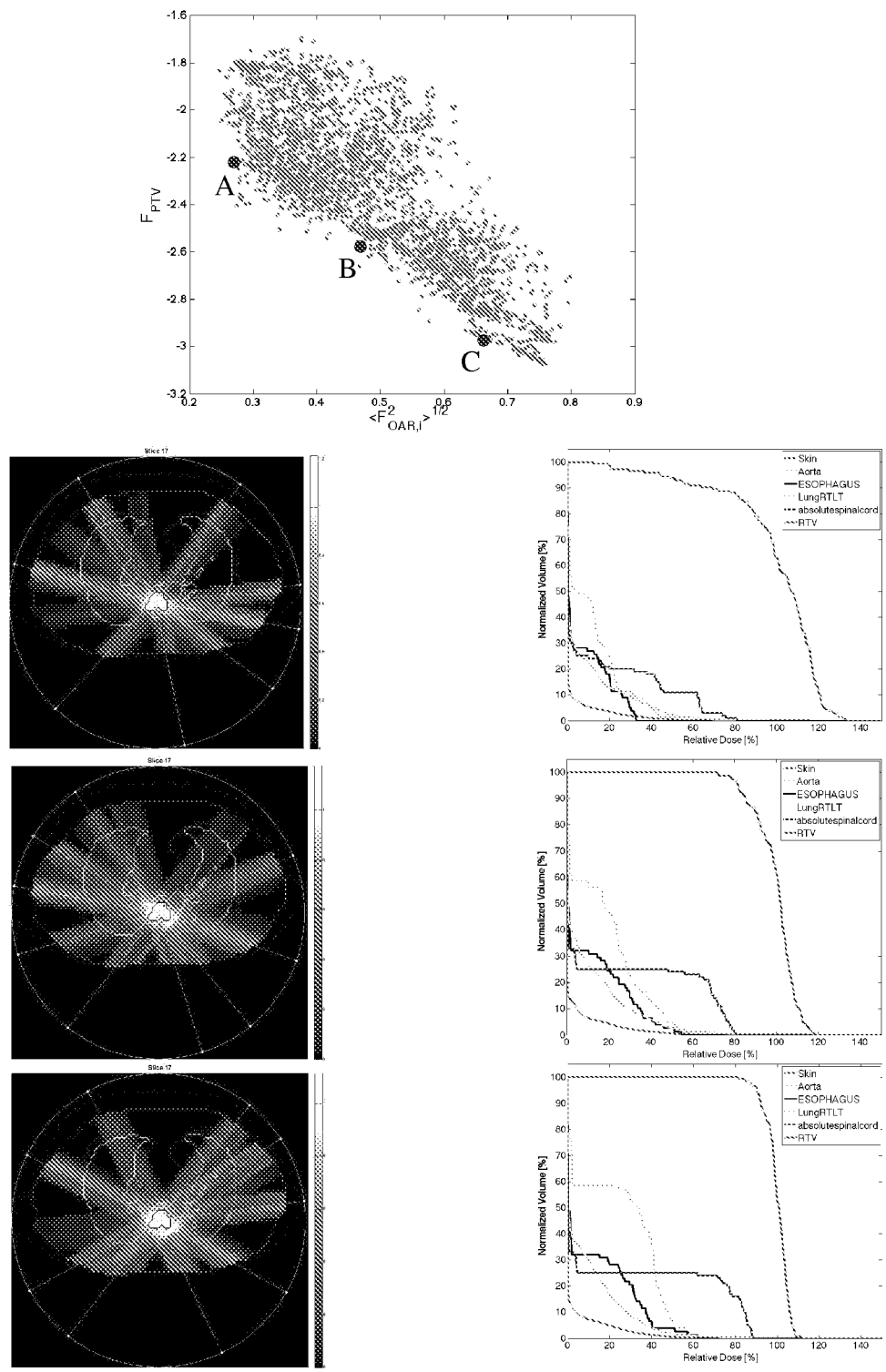
FIG. 13 is a representation of the Pareto non-dominated solution set obtained from a PARETO run using the patient data set with uniform linear attenuation coefficient and solutions evaluated using the PTV-CONF-HOTSPOT fitness function, the F-OAR-DVH (dose threshold=25%) fitness function, and hotspot suppression penalty function #2 with beam merging enabled, followed by images of the radiation dose patterns and DVH curves for three sample solutions.

FIG. 13 shows a projection of the trade-off surface, where the OAR fitness values have been averaged in quadrature for display purposes. The figure also shows axial projections of the radiation pattern and corresponding DVH curves for three different solutions that are shown on the trade-off surface. The trade-offs between conformity and OAR dose are clear from this test, as the PTV conformity improves markedly (flatter PTV DVH with a sharper fall-off) as greater OAR dose is allowed.

10.4. A Realistic Test Problem Using Patient Data with Non-Homogeneous Attenuation Coefficient Obtained from Computed Tomography Data A linear attenuation coefficient matrix can be obtained from the CT DICOM file format after being converted from Hounsfield units used by the DICOM standard. The resulting information is used by the ray tracer/caster to give a more accurate estimate of the dose proxy in the phantom or patient optimization.

A CT DICOM file is read into PARETO following the DICOM file format standard. From this the CT images are obtained into a matrix where each voxel represents a unscaled Hounsfield unit. The following information is also obtained from the DICOM file:
1. pixel spacing
2. image position (patient) representing in millimeters the location of the first voxel
3. image orientation (patient) representing the direction cosines of the first row and column with respect to the patient
4. patient position representing the patient position with respect to the imaging equipment
5. rescale slope and intercept represent values to rescale the Hounsfield units stored in DICOM The resulting image data is then rotated from the standard DICOM left-posterior-superior (LPS) coordinate system to the coordinate system of PARETO.

The DICOM image is generally larger than the treatment volume. Since the full volume is not used, only the maximum dimensions to fit the contoured ROI(s) to the optimization is extracted from the image so that there is a one to one correspondence between voxel location in the image matrix and phantom/patient binary mask matrix created in PARETO's preProcessing routines.

The Hounsfield unit matrix Hounsfield_raw is rescaled and then converted to a linear attenuation coefficient matrix muMatrix according to the following equations:

$$hounsfield=Hounsfield\_raw*ctInfo.RescaleSlope+ctInfo.RescaleIntercept;$$

$$muMatrix=(hounsfieldRescaled.*muWater./1000)+muWater;$$

where ctInfo.RescaleSlope and ctInfo.RescaleIntercept are numerical factors that are encoded with the CT data, and muWater is the linear attenuation coefficient of water. This equation is evaluated for a set of energies $\{E_i\}$ that sample the polyenergetic spectrum of the beam. The resultant muMatrix is therefore represented as a four-dimensional data structure (x,y,z,E) that is passed to the ray tracer.

Figure 14:
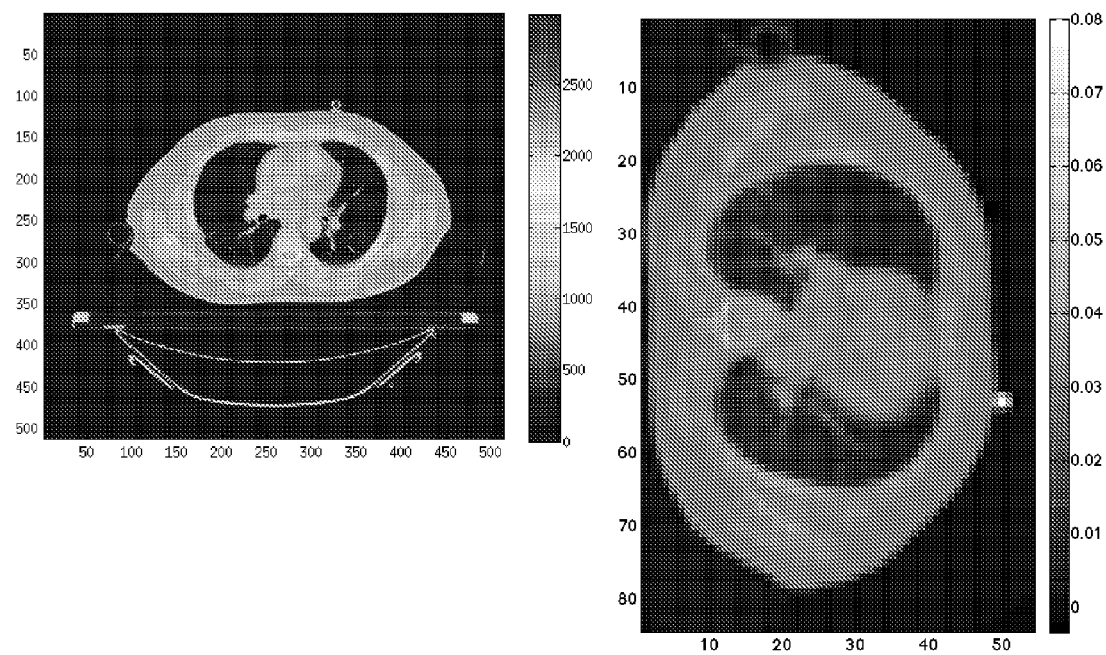
FIG. 14 is comprised of an image showing an axial slice of raw computed tomography (CT) data loaded from a DICOM file corresponding to the patient data set, followed by an image of the CT data converted to linear attenuation coefficient after binning to lower resolution.
Figure 15:
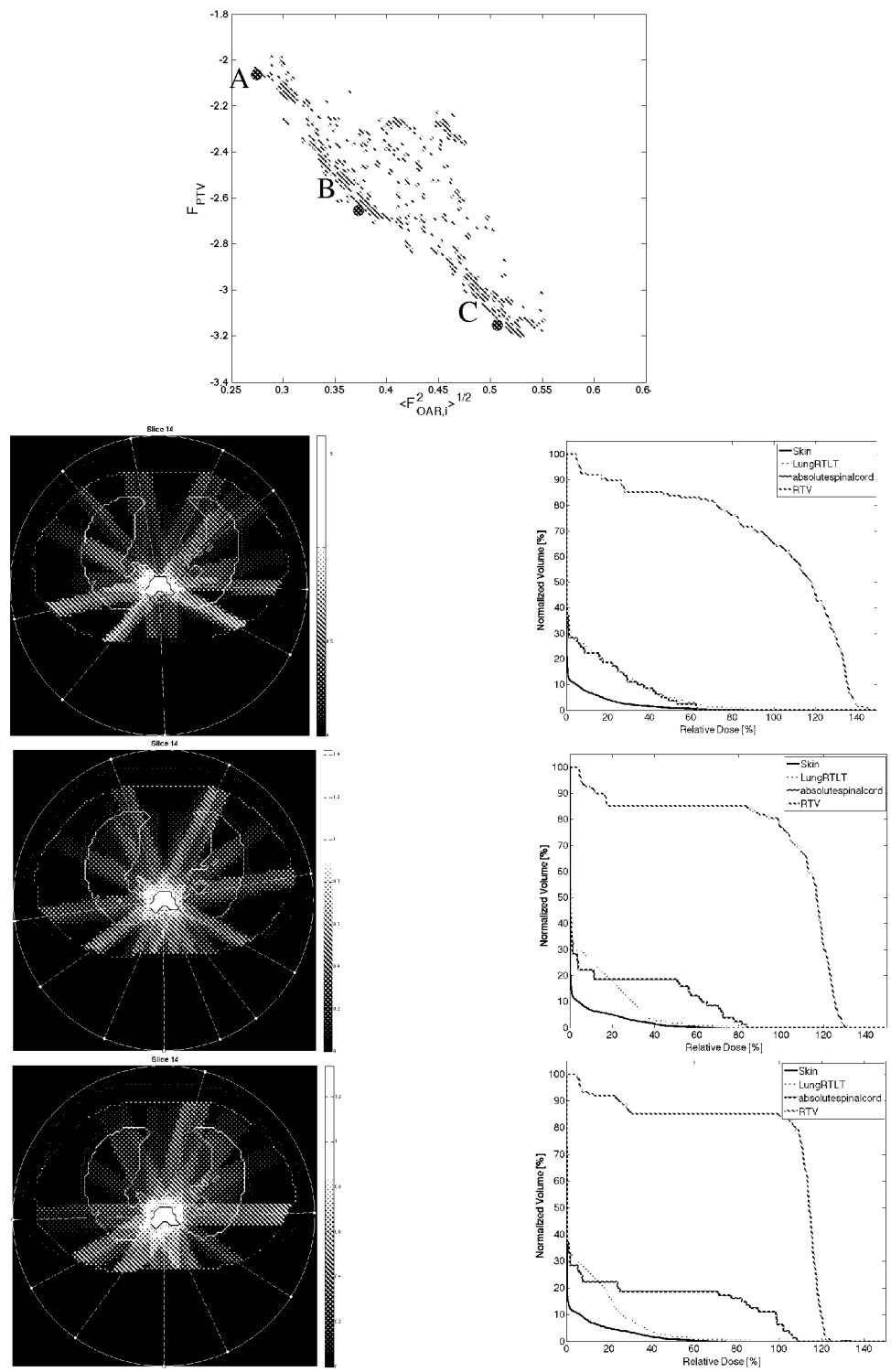
FIG. 15 is a representation of the Pareto non-dominated solution set obtained from a PARETO run using the patient data set with variable linear attenuation coefficient calculated from the CT data and solutions evaluated using the PTV-CONF-HOTSPOT fitness function, the F-OAR-DVH (dose threshold=25%) fitness function, and hotspot suppression penalty function #2 with beam merging enabled, followed by images of the radiation dose patterns and DVH curves for three sample solutions.

To allow for different binning factors that the user may choose for the phantom/patient binary masks, a new grid is formed using the binned data pixel sizes and the linear attenuation coefficient table/matrix is then interpolated down to the new size. FIG. 14 shows the raw data loaded from the DICOM CT image and rescaled data that has been converted to a linear attenuation coefficient by the above procedure FIG. 15 shows a projection of the trade-off surface, where the OAR fitness values have been averaged in quadrature for display purposes. The figure also shows axial projections of the radiation pattern and corresponding DVH curves for three different solutions that are shown on the trade-off surface. More complex patterns are visible in the fine structure of the dose distribution due to the variability of the attenuation coefficient throughout the treatment volume. The trade-offs between conformity and OAR dose are clear from this test, as the PTV conformity improves markedly (flatter PTV DVH with a sharper fall-off) as greater OAR dose is allowed. The variable attenuation coefficient makes it difficult to achieve uniform PTV dose in this example.

11. Algorithm Details, Discussion, and Detailed Testing of PARETO on Artificial Data I. Introduction The objectives of intensity-modulated radiation therapy (IMRT) planning are to deliver a uniform prescribed dose of radiation to one or more planning target volumes (PTVs), while also minimizing the dose to each organ-at-risk (OAR). These clinical objectives are invariably in conflict, often requiring compromises when selecting the best treatment plan for a particular patient. Commercially available approaches to optimizing IMRT plans simplify the problem into a single objective function through the use of relative weighting factors applied to the individual dose-objective terms. In clinical practice, human operators (i.e. treatment planners or dosimetrists) commonly optimize beam orientations manually, add or subtract dosimetric objectives, and vary the weights applied to the dosimetric objectives in a time-consuming, trial-and-error process, attempting to find some acceptable compromise. This simplification ignores the true multiple objective nature of the problem and introduces bias by the choice of weights.

In a multi-objective IMRT treatment planning approach, one would like to simultaneously discover many solutions that sample the Pareto front, which represents the optimal set of feasible compromises between competing objectives defined by the property that it is not possible to improve any objective without degrading at least one other objective. We propose a novel method that uses a multi-objective genetic algorithm (GA) to solve the multi-objective problem without combining weights. Although our heuristic optimization method cannot guarantee strict mathematical Pareto-optimality, we find solutions of high quality in practice, which are very consistent between runs. Moreover, our approach requires no human interaction during the optimization process and scales well to problems with many objectives, which may limit the traditional epsilon-constraint method as discussed below. Thus, our method offers a practical alternative to manual beam angle optimization and automated methods that rely on optimizing a single-objective function with appropriate constraints.

A common approach to multi-objective optimization is to optimize a single-objective function constructed from the weighted sum of multiple objectives. Regions of the Pareto front can be mapped by repeatedly optimizing the weighted function while varying the weight vector between optimizations. However, it has been shown that this approach (without the inclusion of additional constraints) cannot discover optimal solutions on a non-convex region of the Pareto front (Deb, K., *Multi-Objective Optimization using Evolutionary Algorithms*. John Wiley & Sons, ISBN—10: 047187339 X, ISBN—13:9780471873396, 2001.). Both convex and non-convex regions can be discovered by the epsilon constraint method, which optimizes a single objective (or weighted sum of objectives) from a multi-objective problem, while constraining objectives. In this approach, one minimizes a scalar weighted function $\Phi(f(x)) \equiv \Phi(f_1(x), \ldots, f_m(x))$ of the m objectives $f_i$ specified over n parameters $\{x_1, \ldots, x_n\}$ bounded by $x_{j,min} \leq x_j \leq x_{j,max} \forall j \in \{1, \ldots, n\}$ and subject to constraints $f_i(x) \geq \epsilon_i \forall i \in \{1, \ldots, m\}$ where $\epsilon_i$ is the constraint on $f_i$. However, mapping the Pareto front with such a method requires iterative stepping through a grid of constraints while a separate constrained optimization is performed at each step. This may be inefficient for problems with many objectives, and the step size in $\epsilon_i$ must be chosen carefully to achieve the desired resolution of the Pareto front, whose structure is not known a priori.

The need for non-convex solvers becomes an important issue when beam angles or arc-orientations are optimized simultaneously with fluence parameters. Beam fluence optimization is a convex problem for some commonly used objective functions (Deasy, J. O., *Multiple local minima in radiotherapy optimization problems with dose-volume constraints*. Med Phys, 1997. 24(7): p. 1157-61), while the inclusion of beam angles into the optimization process is known to be a non-convex problem (Pugachev, A. B., A. L. Boyer, and L. Xing, *Beam orientation optimization in intensity-modulated radiation treatment planning*. Med Phys, 2000. 27(6): p. 1238-45). We use a sophisticated multi-objective general-purpose GA called Ferret in this work, which is designed to solve both convex and non-convex problems, as illustrated by several examples included with the software and described in its user's guide. Ferret evolves a population of trial solutions over many generations, while maintaining an internal Pareto ranking of solutions. The set of non-dominated solutions is saved to disk each generation, where a non-dominated solution is one where no other solution exists within the current population that is superior in all objectives. These solutions are reloaded at the end of the run and compared against each other to construct a final set of globally non-dominated solutions, which approximates the Pareto surface for many test problems.

The concept of multi-objective optimization for radiotherapy treatment planning has been an active area of research. Various approaches including simulated annealing optimization (Aubry, J. F., et al., *Multiobjective optimization with a modified simulated annealing algorithm for external beam radiotherapy treatment planning*. Med Phys, 2006. 33(12): p. 4718-29), multi-objective rotational therapy optimization (Fenwick, J. D. and J. Pardo-Montero, *Homogenized blocked arcs for multicriteria optimization of radiotherapy: analytical and numerical solutions*. Med Phys, 2010. 37(5): p. 2194-206; Pardo-Montero, J. and J. D. Fenwick, *An approach to multiobjective optimization of rotational therapy*. Med Phys, 2009. 36(7): p. 3292-303), combining optimization sequences in real-time (Das, S. K., *A method to dynamically balance intensity modulated radiotherapy dose between organs-at-risk*. Med Phys, 2009. 36(5): p. 1744-52), convex multi-objective fluence map optimization (Craft, D. and T. Bortfeld, *How many plans are needed in an IMRT multi-objective plan database?* Phys Med Biol, 2008. 53(11): p. 2785-96; Craft, D., et al., *Exploration of tradeoffs in intensity-modulated radiotherapy*. Phys Med Biol, 2005. 50(24): p. 5857-68; Craft, D., et al., *An approach for practical multiobjective IMRT treatment planning*. Int J Radiat Oncol Biol Phys, 2007. 69(5): p. 1600-7; Craft, D. and M. Monz, *Simultaneous navigation of multiple Pareto surfaces, with an application to multicriteria IMRT planning with multiple beam angle configurations*. Med Phys, 2010. 37(2): p. 736-41; Hoffmann, A. L., et al., *Derivative-free generation and interpolation of convex Pareto optimal IMRT plans*. Phys Med Biol, 2006. 51(24): p. 6349-69; Hong, T. S., et al., *Multicriteria optimization in intensity-modulated radiation therapy treatment planning for locally advanced cancer of the pancreatic head*. Int J Radiat Oncol Biol Phys, 2008. 72(4): p. 1208-14; Monz, M., et al., *Pareto navigation: algorithmic foundation of interactive multi-criteria IMRT planning*. Phys Med Biol, 2008. 53(4): p. 985-98; Spalke, T., et al., *Analyzing the main trade-offs in multiobjective radiation therapy treatment planning databases*. Phys Med Biol, 2009. 54(12): p. 3741-54; Thieke, C., et al., *A new concept for interactive radiotherapy planning with multicriteria optimization: first clinical evaluation*. Radiother Oncol, 2007. 85(2): p. 292-8), beam profile and voxel weight multi-objective optimization subject to soft and hard constraints (Breedveld, S., et al., *A novel approach to multi-criteria inverse planning for IMRT*. Phys Med Biol, 2007. 52(20): p. 6339-53), and conjugate gradient multi-objective optimization (Cotrutz, C., et al., *A multiobjective gradient-based dose optimization algorithm* for external beam conformal radiotherapy. Phys Med Biol, 2001. 46(8): p. 2161-75) have been studied. Schreibmann et al. (Schreibmann, E., et al., *Multiobjective evolutionary optimization of the number of beams, their orientations and weights for intensity-modulated radiation therapy*. Phys Med Biol, 2004. 49(5): p. 747-70; Schreibmann, E. and L. Xing, *Feasibility study of beam orientation class-solutions for prostate IMRT*. Med Phys, 2004. 31(10): p. 2863-70) investigated multi-objective optimization of the number of beams, their orientations, and intensity profiles. Their approach used a GA to perform an outer loop optimization over beam angles, while optimizing beam profiles for each set of beam angles using a gradient-based algorithm in an inner loop. We propose a simpler approach that treats beam angles and fluence parameters as part of a single, monolithic, multi-objective optimization problem. This approach is efficient because it does not require division of the problem into inner and outer optimizations, but a powerful optimizer is required to avoid local minima in the enormous search space.

We introduce a new software package named PARETO (Pareto-Aware Radiotherapy Evolutionary Treatment Optimization), which uses the Ferret GA to optimize this difficult multi-objective problem. PARETO and Ferret operate at arm's length; PARETO is entirely responsible for the specification of the radiotherapy problem and the evaluation of the fitness functions, while Ferret functions as a black box optimizer whose role is to choose "good" parameters for PARETO to evaluate without any internal knowledge of the radiotherapy problem. We describe the evolutionary optimizer used to solve the monolithic radiation treatment planning problem in Section II.A and provide an overview of PARETO in Section II.B. We discuss our methodology for comparing with a commercial treatment planning system in Section II.C and show an actual comparison in Section III.A. In Section III.B, we compare several different choices of fitness functions (i.e. objective functions) currently implemented within PARETO for a simple phantom geometry and coplanar beam arrangements. Section III.C. explores the usefulness of PARETO for selecting the best number of beams used for treatment. We discuss our results in Section IV, where we also indicate PARETO's current limitations and plot a course toward a feasible tool for clinical use. Final conclusions are provided in Section V.

II Method and Materials

A. The Ferret Genetic Algorithm

The solution to a multi-objective optimization problem is given by the set of points residing on a multi-dimensional Pareto front (or trade-off surface) of dimensionality $N_{obj}-1$ for a problem with $N_{obj}$ non-degenerate objective functions. For example, the Pareto set of a dual objective problem usually forms a curve in the objective and parameter spaces, which may be continuous or piecewise continuous. Likewise, the solution set to a problem defined by three objectives normally spans a two-dimensional curved surface. Multi-objective optimizers strive to sample the Pareto front with solutions, which represent the best compromises possible between competing objectives.

GAs are an important class of algorithms for global optimization that work in analogy to biological evolution. A basic GA encodes parameters on "genes", which are expressed as a model (or individual) and evaluated by a fitness function. A population of such models evolves over multiple generations by applying mutation, crossover, and selection operators, which are designed to explore the parameter space and gradually improve the fitness of the population. The role of mutation is to apply occasional random perturbations to individuals, which helps the algorithm to explore new regions of the parameter space. Crossover combines two individuals to produce offspring that are intermediate between the parent models. The selection operator is an information filter based on the Darwinian notion of survival of the fittest, which preferentially selects fit individuals to propagate to the next generation, while destroying weaker individuals. Various types of selection operators are possible, but tournament selection has the advantage that it is insensitive to the scaling of the fitness functions.

The Ferret GA is a parallel multi-objective GA that has been under development since 2002. Ferret provides a thorough exploration of PARETO's parameter space and the ability to map trade-off surfaces between its multiple objective functions, which allows the user to understand the compromises that must be made during treatment planning. The interface provides an indication of convergence by graphically monitoring the number of solutions present in the per-generation non-dominated set, the median rank of the population, and the minimum value achieved for each objective. We ran the code far past apparent convergence for all results presented here, which has the effect of increasing the number of solutions in the optimal set. As discussed briefly in the previous section, this optimizer constructs a final database of non-dominated solutions at the end of a run by reloading all saved solutions that were non-dominated within their own generation, comparing them against each other iteratively, and rejecting any solution that is dominated by a solution from another generation. The database is guaranteed to be a non-dominated set constructed from thousands of trial solutions explored during the run. This non-dominated set is not proven mathematically to coincide with the Pareto surface, but in practice we find solutions that compare favourably with those found from commercial treatment planning systems. Results are almost perfectly consistent between runs, which is encouraging because such consistency would be unlikely for a stochastic optimizer struggling to find the Pareto surface and becoming trapped by false solutions far from Pareto-optimality.

Ferret uses a niching algorithm similar to the one discussed by Fonseca et al. (Fonseca, C. M., *Genetic Algorithms for Multiple Objective Optimization: Formulation, Discussion and Generalization. in [ICGA5]*, pp. 416-423, 9993) to spread PARETO's solutions approximately uniformly over the final optimal set. A niching algorithm measures the Euclidean distance, in either parameter or objective space, between trial solutions at each generation and calculates a niche count for each solution, which is given by the number of near neighbors within a pre-defined niching radius. The Pareto rank of a solution is given by $R=1+N_{sup}$, where $N_{sup}$ is the number of superior (dominating) solutions present, such that $R=1$ for the non-dominated set. Ties in rank are common in a multi-objective GA when two solutions compete in tournament selection. When ties occur, the diversity of the population is improved by keeping the solution with the lower niche count, since it resides in a less well-represented (and probably less well-explored) region of the parameter or objective space. PARETO was configured to perform niching in objective space for all results presented.

PARETO makes extensive use of other features in Ferret that further extend the basic GA paradigm for parameter search and global optimization. For instance, this GA contains a machine-learning algorithm that monitors optimization progress to automatically adapt the mutation scale, the size scale of crossover events, and several other important control parameters in order to improve the search in response to the fitness landscape. Auto-adaptation provides an extra layer of robustness to PARETO by making the search less sensitive to the GA's internal control parameters (strategy parameters). GAs are well suited for parallel computing because each individual in the population represents a single parameter set, which can be evaluated independently of other parameter sets. PARETO takes advantage of Ferret's internal parallelization, which dramatically speeds up runs performed on multi-CPU computers and inexpensive clusters. Ferret is part of the Qubist Global Optimization Toolbox, which is distributed by nQube Technical Computing Corporation (Winnipeg, Canada). Older versions of the code (Fiege, J. D., et al., *A Genetic Algorithm-based Exploration of Three Filament Models: A Case for the Magnetic Support of the G11.11-0.12 Infrared-dark Cloud*. Ap. J., 2004. 616: p. 925-942; Fiege, J. D., *Computational intelligence techniques for submillimeter polarization modeling*, in ASP Conf. Ser. 343, *Astronomical Polarimetry Current Status and Future Directions*, ed. A. J. Adamson et al. (San Francisco: ASP). 2005: p. 171-175) and the current version (Baran, A., *Foreground Detection with the DRAO Synthesis Telescope: Methods and Models to Measure the Polarized Cosmic Microwave Background*. M.Sc. thesis, University of Manitoba, 2010; Rogers, A. and J. D. Fiege, *Gravitational Lens Modeling with Genetic Algorithms and Particle Swarm Optimizers*. Ap. J., submitted 2010) have been used for various problems in astronomy and astronomical instrumentation.

B. An Overview of PARETO

Early versions of PARETO focused on geometric optimization methods that minimized the volume-weighted average number of beams that intersected OARs (Potrebko, P. S., et al., *A Simple Geometric Algorithm to Predict Optimal Starting Gantry Angles Using Equiangular-spaced Beams for Intensity Modulated Radiation Therapy of Prostate Cancer*. Med Phys, 2007 34(10): p. 3951-3961). Geometry-based fitness functions are attractive because they can be computed much more rapidly than dose-based methods. Rapid evaluation is especially important for our approach, since Ferret typically requires $10^4$ to $10^5$ evaluations of the fitness functions to optimize problems involving more than about five parameters, with the required number of evaluations increasing only very slowly with the size of the problem. However, purely geometric methods were abandoned because they did not produce consistently better plans than manual approaches at some treatment sites.

The current version of PARETO utilizes ray-tracing methods to calculate the primary dose, including divergence, attenuation, and inverse-square law effects, which is then convolved with a scattering kernel to simulate patient scatter (Ahnesjo, A., *Collapsed cone convolution of radiant energy for photon dose calculation in heterogeneous media*. Med Phys, 1989. 16(4): p. 577-92). Rays are assumed to be conformal to the projection of the PTV in the beam's-eye-view (BEV) plane, and are modulated by a parameterized fluence pattern at each beam angle. We initially attempted to optimize fluence patterns by solving an inner loop fluence optimization problem for each pair of beam angles ($\theta$, $\phi$) sampled by the GA during the optimization process, where $\theta$ and $\phi$ represent the gantry and couch angles respectively. However, this inner/outer loop approach is impractical because the total number of evaluations scales as the product of the number of evaluations required for convergence of the inner and outer problems separately. It is more efficient to instead treat beam angle selection and fluence modulation as a single monolithic optimization problem, with all beam angles and fluence parameters handled in exactly the same way, and optimized simultaneously by the GA.

Naturally, a monolithic formulation increases the dimensionality of the optimization problem, which requires an optimizer that performs well on very large problems. Nevertheless, it is beneficial to reduce the number of parameters required to model each fluence pattern where such reduction is possible. At present, we model the fluence pattern as a linear gradient function that is applied to the projection of the PTV in the beam's-eye-view plane:

$$F_{PTV}=F_0+[g\cdot(x-x_0)], \quad (1)$$

where $x=(x, y)$ is a point within the projected PTV, $x_0$ is the isocentre of the projected PTV, $g=(g_x, g_y)$ is the fluence gradient, and $F_0$ is the fluence offset. The fluence is set to zero for all pixels outside the PTV. Furthermore, the fluence is constrained to the range [0, 1] by setting $F_{PTV}$ to zero anywhere that F<0 and to one wherever F>1. A fluence reduction parameter q is specified for each OAR such that $$F_{OAR}=qF_{PTV}; q\in[0,1] \quad (2)$$

for points that fall within the projected boundary of the OAR. Thus, the overall fluence pattern takes the form of a linear truncated gradient over the PTV, which is reduced by factor q over each OAR, and is zero outside the projected PTV. An advantage of this approach is that it automatically results in smooth fluence gradients within ROIs, and sharp (discontinuous) gradients at their boundaries. This simple parameterization is not as flexible as the non-parametric approach used by commercial IMRT optimizers to model fluence patterns, and at this early stage of development PARETO's fluence patterns are not expected to be as refined. However, for simple test phantoms, our approach provides sufficient modulation comparable to a commercial treatment planning system as shown by the solutions discussed in Section III.A. Our method may be readily extended to include multiple additive gradients for greater modulation. We are currently investigating this and other parameterizations to refine our fluence patterns.

For each beam angle, three parameters are required to model the gradient function, and one additional parameter is required for each OAR. Thus, $(3+N_{OAR})*N_{beam}$ parameters are required to model the fluence pattern, where $N_{OAR}$ is the number of OARs and $N_{beam}$ is the number of beams. The total number of parameters, including beam angles, is given by $N_{par}=(4+N_{OAR})*N_{beam}$ for coplanar beam angle optimizations, and $N_{par}=(5+N_{OAR})*N_{beam}$ for non-coplanar runs. Thirty-five parameters are therefore required for a five beam coplanar problem with three OARs, such as the solutions shown in Section III.B.

Ferret allows parameters to be designated as periodic, such that the minimum and maximum values represent the same configuration. PARETO's gantry angles are treated as periodic, with zero degrees and 360 degrees representing the same position. Couch angles vary from −90 degrees to 90 degrees and are not considered periodic. These ranges map the full sphere containing all possible beam angle orientations. Since the order in which beams are applied does not matter, it is beneficial to reduce the size of the search space by sorting beams first by gantry angle, and second by couch angle when a pair of beams shares the same gantry angle. This sorting operation is non-trivial because fluence parameters must also be re-arranged when the beam order changes. Ferret was customized for PARETO by adding a re-insertion mechanism that allows these modified parameters to be placed back into the GA population.

PARETO can be run in a mode that allows beams to merge when their angular separation on a sphere defined by $(\theta, \phi)$ is less than a threshold value, which is typically 10 to 15 degrees. PARETO performs a binary search that identifies and merges beams closer than the threshold angle, in order of increasing angular separation, and stops when no two beams are closer than the threshold. A beam merger averages the vector position of two beams on the unit sphere and also averages their fluence maps prior to the evaluation of the fitness function. Merging results in two identical beams. However, PARETO ignores duplicate beams by sending only one copy of the merged pair to the fitness functions. It is a subtle point that beam angles modified by merging are evaluated 'on the fly' by the fitness function, but are not re-inserted back into the GA population via the parameter re-insertion mechanism used for beam sorting. Merging beams results in the duplication of parameters, which would severely degrade the diversity of parameter values present in the population and damage the search if re-insertion were allowed. Note that beam merging is fundamentally different from beam sorting, which does not result in parameter duplication and helps the search by decreasing the size of the parameter space. The beam merging feature was added to allow preliminary evaluation of PARETO's ability to optimize the number of beams in addition to beam angles and fluences.

It is a significant challenge to develop realistic multi-objective fitness functions for the OARs and the PTV. These fitness functions are used by the GA as the sole measures of solution quality, and therefore must robustly encode the attributes of the dose distribution as would be judged by a dosimetrist. The assessment must be compressed into a single number for each OAR or PTV. Table I lists the fitness functions for the OARs and PTV, which are currently implemented in PARETO. We note that Ferret is a minimizer and therefore good solutions correspond to low values of the fitness function. The choice of the OAR and PTV fitness functions strongly affects the character and quality of solutions. We have studied their behaviour with a simple homogeneous cylindrical phantom (FIG. 4). In the remainder of this section we describe the fitness functions studied here and discuss some of the rationale behind their selection.

Earlier versions of PARETO used a combination of the PTV dose standard deviation (F-PTV-STD) and simple OAR mean dose (F-OAR-SIMPLE) fitness functions. The F-OAR-SIMPLE function places too much emphasis on reducing dose below normal thresholds and very few balanced solutions were discovered using this function. Solution sets typically contained a few good solutions, but these were diluted by a large number of poor solutions characterized by extremely low dose for one or more OARs, but unacceptably high dose for other OARs and poor PTV uniformity. This problem is remedied by fitness functions that include a dose threshold $D_0$ for each OAR, as discussed below. The F-PTV-STD fitness function resulted in a poor spatial distribution of beams. With this PTV fitness function, PARETO typically reduced the effective number of beams by causing pairs of beams to overlap while decreasing the intensity of each. However, these solutions suffered from a serious defect characterized by poor conformity to the PTV. Severe hotspots of dose exterior to the PTV were not suppressed because the uniformity fitness function computed the standard deviation of the dose over the PTV only, without considering voxels outside.

The development of the PTV conformity fitness function (F-PTV-CONF) resolved the problem of external hotspots by encouraging better spacing of beams. The conformity fitness function is based on the statistical correlation function between the dose D and a mask M, over all voxels within the treatment region. The mask corresponds to a perfect dose distribution, with a value of one assigned to voxels within the PTV, and a value of zero assigned outside the PTV. This function is especially useful in that it formulates two objectives: the conformity of the dose distribution to the PTV structure, and the reduction of hotspots external to the PTV. Thus, the dimensionality of the solution set is reduced, which simplifies the analysis and reduces the complexity of the problem. The conformity function is designed to allow variable weighting between the PTV and the exterior. Weighting was included because we find in general that equal weighting between the PTV and exterior overemphasizes the exterior, where excellent suppression of hotspots is achieved, but at the cost of poor PTV uniformity. This problem is alleviated by placing more weight on the PTV as the exterior by setting:

$$w_i \approx \begin{cases} w_{PTV}, & PTV \text{ voxels} \\ 1 - w_{PTV}, & \text{outside} \end{cases} \quad (3)$$

where we have chosen $w_{PTV}=5/7$ in this work. It is possible within our framework to eliminate this weighting by splitting the conformity fitness function into two separate uniformity objectives for regions interior and exterior to the PTV. However, the increased complexity is not warranted because our solutions are only weakly sensitive to $w_{PTV}$.

Better spacing of beams was noted for the F-PTV-CONF and F-OAR-SIMPLE combination of fitness functions compared to those found using the F-PTV-STD and F-OAR-SIMPLE combination. However, very few balanced solutions were present in the non-dominated set. Some OARs were driven to very low dose at the expense of others, and the PTV uniformity was poor for most solutions.

Dose-volume histograms (DVHs) are used universally to assess the quality of treatment plans. Therefore, PARETO implements a DVH-based fitness function (F-OAR-DVH in Table I) to simulate this decision process. This fitness function is based on the mean DVH-weighted dose, normalized to the mean PTV dose and modified by dose threshold $D_0$ for each OAR. Results are dependent on the dose threshold, which must be chosen carefully to reflect realistic targets for OARs. Choosing thresholds that are too low results in a non-dominated set populated with many clinically unacceptable solutions with targets that cannot be achieved and poor PTV uniformity, much like our experiments with the F-OAR-SIMPLE function discussed above. Naturally, we would prefer more general fitness functions that do not require dose thresholds as extra free parameters. However, well-chosen thresholds are necessary in the present implementation. Additionally, an exponent p affects the emphasis placed on suppressing high dose voxels, such that $p=1$ is an appropriate choice for parallel structures, while $p>1$ more strongly suppresses small regions of high dose, and therefore may be more appropriate for serial structures.

PARETO also implements a fitness function labeled as F-OAR-EUD in Table I, which is based on the equivalent uniform dose (Niemierko, A., *Reporting and analyzing dose distributions: a concept of equivalent uniform dose*. Med Phys, 1997. 24(1): p. 103-10). The similarity to the simple OAR fitness function is obvious, except that a dose threshold $D_0$ and a dose exponent p are implemented in the same manner as the DVH fitness function. The normalized equivalent uniform dose function is more biologically motivated than the DVH fitness function, although the DVH function may more closely reflect the decision process of a clinician. Both produce solutions of excellent quality that are of similar character as discussed in Section III.B. Several metrics are used to evaluate plan quality including: the standard deviation of dose within the PTV structure, the maximum point dose (hot spot) outside the PTV structure, and the radiation conformity index (Knoos, T., I. Kristensen, and P. Nilsson, *Volumetric and dosimetric evaluation of radiation treatment plans: radiation conformity index.* Int j Radiat Oncol Biol Phys, 1998. 42(5): p. 1169-76) of the 95% isodose surface, $RCI_{95}$ (defined as the volume of the PTV divided by the volume of the 95% isodose surface, with the 95% isodose surface completely encompassing the PTV).

The preferred OAR fitness functions within PARETO (F-OAR-DVH and F-OAR-EUD) both implement a target dose threshold, which appears to be the main factor responsible for their superiority compared to the F-OAR-SIMPLE function. The GA works to decrease OAR fitness values only until the dose targets are achieved, usually early in the run for most solutions, and then focuses almost exclusively on the PTV fitness function late in the run. This results in a large population of well-balanced solutions in the final non-dominated set that simultaneously achieve realistic dose thresholds and maximize PTV uniformity.

C. Methodology for Comparison with a Commercial Treatment Planning System

This section describes the methodology used to compare solutions from PARETO with the Eclipse treatment planning system (Varian Medical Systems, Palo Alto, Calif.). PARETO's multi-objective optimization approach is fundamentally different from the single-objective approach used in existing commercial treatment planning systems such as Eclipse. In addition, the fitness functions in Table I are designed specifically for PARETO, and differ from the weighted terms used for single-objective optimization. We therefore expect a correlation between DVHs computed by PARETO and commercial systems, but not exact quantitative agreement. The F-OAR-DVH fitness function in Table I is especially useful for this comparison because it can be applied to both PARETO solutions and DVH data exported from Eclipse. In order to compare PARETO solutions with those computed from Eclipse, we search through the PARETO solution database to find a multi-objective solution that achieves the set dose threshold $D_0$ for all OARs. We then define the objective dose as $D_0$ for each OAR in Eclipse, input the beam angles from the selected PARETO solution, and optimize the fluence. We export the DVH data from Eclipse for comparison with DVH curves computed using PARETO.

III. Results

For the results presented here, we used an exponent of p=1 for the F-OAR-DVH and F-OAR-EUD fitness functions. A total population size of 300 was used for the GA, which optimized for 1000 generations, requiring several hours of computation in parallel on a server with twelve CPU cores. The run appeared to converge after the first 100 to 200 generations, with no further improvement in OAR fitness values and only small improvements of a few percent in the PTV fitness. The non-dominated set was essentially stable at this point, with the remaining generations serving to increase the number of solution points and provide slight refinement.

A. Comparison with a Commercial Treatment Planning System

Figure 5:
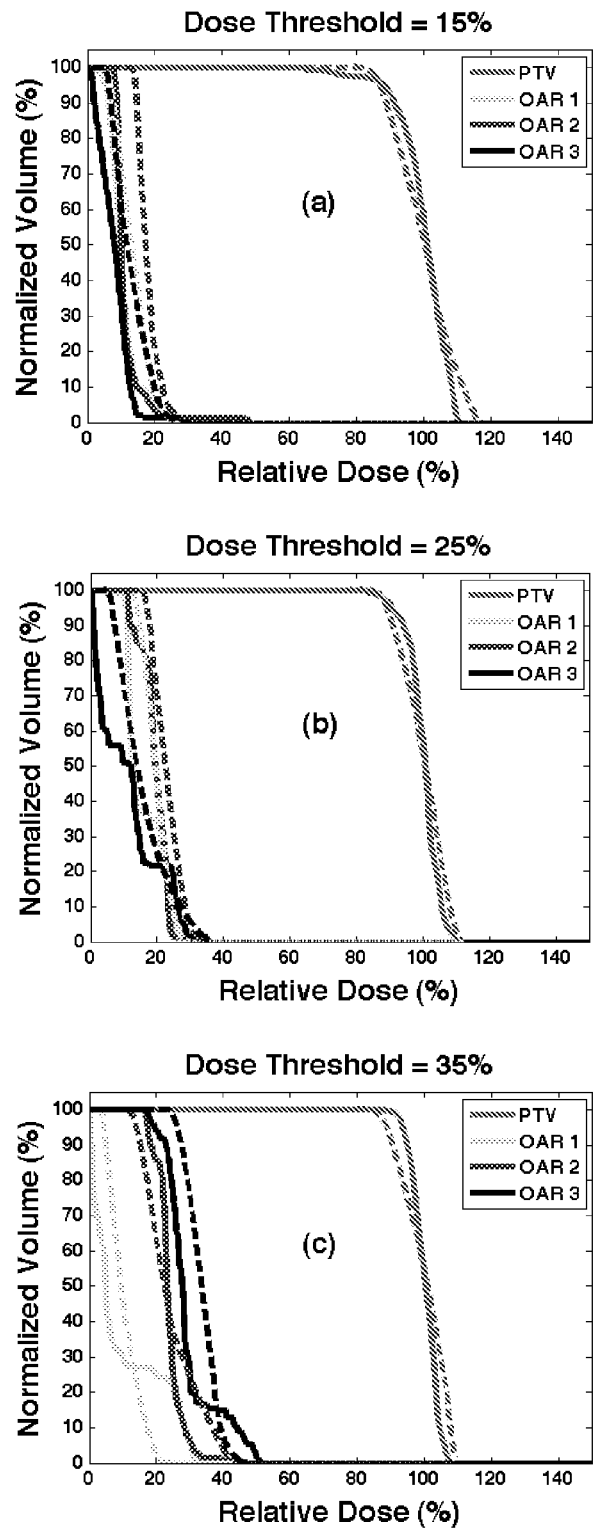
FIG. 5 is comprised of a set of DVH curves comparing PARETO treatment plans computed for three different OAR dose thresholds using the F-PTV-CONF-HOTSPOT and the F-OAR-DVH fitness functions to treatment plans computed using the Eclipse commercial treatment planning system.

FIG. 5 demonstrates a good correlation between PARETO and Eclipse dose-volume histograms for dose thresholds of $D_0$=0.15, 0.25, and 0.35. We performed a PARETO run for each of these dose thresholds, selected an optimized solution from the trade-off surface, and the PARETO-optimized beam angles were input manually into Eclipse for comparison. PARETO appears to find solutions offering comparable sparing of the OARs and superior uniform coverage of the PTV. However, we note that PARETO does not yet take into account MLC sequencing, which might cause some degradation of solution quality. The comparison between PARETO and Eclipse may be strengthened by improving PARETO's dose calculation accuracy through the use of a two-source linear accelerator head fluence model including MLC modeling, and conversion of ideal fluence maps to deliverable MLC sequences.

B. Comparison of Fitness Functions

1. OAR DVH Fitness Function with PTV Conformity Fitness

FIG. 6 shows the final non-dominated set projected into the plane of the F-PTV-CONF fitness function and the quadrature-averaged F-OAR-DVH fitness functions. We note that the quadrature average is used for visualization purposes only; the OAR fitness functions were not combined during the multi-objective optimization. Each data point represents a non-dominated plan. Dose distributions and DVHs for three highlighted plans (A, B, C) are shown. A dose threshold of $D_0$=0.25 was used. The maximum dose in other healthy tissue (OHT) was 103%, 112%, 103%, the PTV dose standard deviation was 0.10%, 0.043%, 0.042%, and the radiation conformity index of the 95% isodose volume ($RCI_{95}$) was 1.27, 1.09, 1.06 for solutions A, B, C, respectively. Using this combination of fitness functions, the PTV dose is relatively uniform and conformal, beams are well spread out, and no hotspots are apparent (FIG. 6).

2. Normalized OAR EUD Fitness Function with PTV Conformity Fitness

We find that solutions using the EUD fitness function (FIG. 7) are very similar to those computed using the DVH fitness function. The maximum OHT dose was 107%, 113%, 109%, the PTV dose standard deviation was 0.11%, 0.060%, 0.054%, and the $RCI_{95}$ was 1.40, 1.13, 1.14 for solutions A, B, C, respectively. In this case, a dose threshold of $D_0$=0.25 was used, however, we note that the EUD fitness function reduces to the simple OAR fitness function when p=1 and $D_0$=0, which confirms that the OAR dose threshold is the main factor responsible for the greatly improved solution quality over the simple OAR fitness function.

C. Treatment Plan Selection

Figure 9:
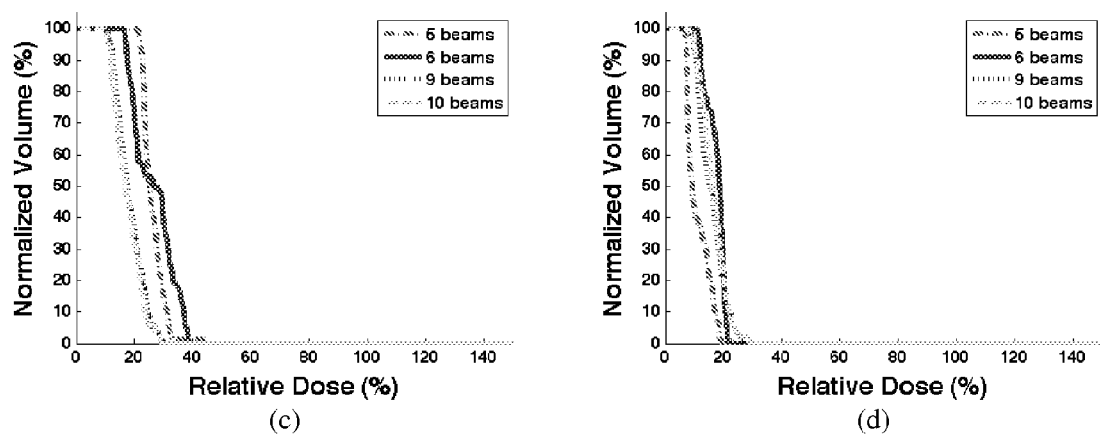
FIG. 9 is a representation of DVH curves for the solutions highlighted in FIG. 8.

In this example, PARETO generated a database of 452 Pareto-optimal solutions using the F-OAR-DVH and F-PTV-CONF fitness functions with a dose threshold of $D_0$=0.25. Beams closer than 15 degrees were merged, and a slight perturbation $\Delta F=10^{-6} N_{beams}$ was added to all fitness functions to slightly prefer solutions with fewer beams, where $N_{beams}$ is the number of unique beams. It is important to note that the Ferret GA uses tournament Pareto ranking; thus, this tiny perturbation is sufficient to strongly prefer solutions with fewer beams late in the run when the population is rich with solutions that achieve their dose thresholds such that $F_{OAR}$=0 for one or more OARs. FIG. 8a shows the final non-dominated set as projected into the plane of the F-PTV-CONF fitness function and the quadrature-averaged F-OAR-DVH fitness functions. Four plans containing ten, nine, six and five unique beam angles are highlighted. FIG. 8b demonstrates a trend of improved dose conformity to the PTV by increasing the number of optimized beams. The maximum OHT dose was 118%, 108%, 111%, 117%, the PTV dose standard deviation was 0.071%, 0.043%, 0.058%, 0.060%, and the $RCI_{95}$ was 1.25, 1.05, 1.18, 1.13 for the ten, nine, six and five beam plans, respectively. A maximum number of eleven beams were specified in PARETO, but the optimizer did not find any significant improvement in the PTV fitness by using more than ten beams. We note that the PTV fitness function is logarithmic, and as such the actual differences in F-PTV-CONF are small at the minimum values for ten and nine beams. FIG. 8b therefore suggests that PTV conformity gradually saturates to a nearly constant minimum value at approximately nine beams, and additional beams provide no significant additional benefit, which is a result similar to earlier work examining the optimal number of beam angles for IMRT (Stein, J., et al., *Number and orientations of beams in intensity-modulated radiation treatments*. Med Phys, 1997. 24(2): p. 149-60). The differences in the OAR fitness values between the four highlighted plans produce a spectrum of DVHs, as shown in FIG. 9.

IV. Discussion

This work demonstrates that PARETO is able to find high quality solutions to the problem of multi-objective IMRT treatment planning. PARETO does not yet optimize fluence patterns as finely as commercial treatment planning systems, but the software's rudimentary linear gradient method is sufficiently flexible to permit the discovery of good beam orientations. Moreover, solutions are rapid to evaluate, and therefore suitable for global optimization with a GA. More sophisticated fluence parameterizations are under development to further improve the PTV dose uniformity and OAR sparing. Our linear gradient fluence parameterization resulted in DVH curves that are comparable to those calculated by Eclipse. However, this comparison must be approached with caution until PARETO is able to model the linear accelerator head fluence, including the MLC, and conversion of optimal fluences to deliverable MLC sequences. Future work will explore these important details.

The end result of a PARETO run is a database of non-dominated solutions that show trade-offs between OAR and PTV fitness functions, typically containing at least $10^3$ solutions, which are all equally good in the Pareto-optimal sense. Thus, good interactive visualization tools are essential to navigate the database to find the best physician-selected plan to treat the patient. We have implemented a preliminary "PARETO Navigator" tool for this purpose, which will be discussed elsewhere. Given the reasonable assumption that the selection of the best plan from the Pareto-optimal database can be made rapidly through a well designed graphical user interface, this implies that PARETO offers a significant improvement in treatment planning efficiency, and therefore will increase patient throughput.

The multi-objective tool developed here has two major implications for clinical treatment planning. The first is that simultaneously optimizing beam angles and fluence patterns by solving the full multi-objective problem may result in better quality solutions than those developed by manual selection of beam angles followed by fluence optimization. The second is that it is possible to streamline treatment planning by providing an automated multi-objective technique, which eliminates the need for iterative, human manipulation of weighting factors and dose objectives during optimization. We emphasize that PARETO does not eliminate the need for human clinical input during treatment planning, but rather shifts the focus to rapid exploration of a pre-optimized set of solutions and expert selection of a treatment plan.

PARETO makes use of Ferret's internal parallelization and run times scale approximately as $N^{-0.8}$, where N is the number of CPU cores employed. Thus, clinically viable optimization times are within reach, given a sufficient number of cores. We are testing a new version of PARETO that uses several graphical processing units (GPUs) to increase the speed of computation. The GPU work will be discussed in a future publication and benchmarked against the current version, which used CPU-based computation only.

V. Conclusions

We have introduced PARETO, a true multi-objective optimization tool to solve the IMRT treatment planning problem. PARETO utilizes a powerful evolutionary algorithm to handle the combined monolithic problem of beam fluence and beam angle optimization. We have employed a simple parameterized beam fluence representation with a realistic dose calculation to demonstrate feasibility for a simple phantom. The combination of the conformity-based PTV fitness function and the DVH or EUD-based fitness functions for the OARs produced acceptably uniform and conformal PTV doses, with well-spaced beams and no hotspots. Results also indicated that PARETO shows promise in optimizing the number of beams. Comparison of resulting DVHs to those from treatment plans developed with a single-objective fluence optimizer (commercial planning system Eclipse) showed a good correlation. Work is underway to develop improved fluence parameterizations that are more flexible than the simple gradient-based method discussed here. Future versions of PARETO will include a linear accelerator head fluence model and MLC sequencer, as the software evolves toward clinical use.

12. Application of PARETO to Stereotactic Body Radiation Therapy (SBRT)

This section is based on an abstract presented at the American Society for Radiation Oncology annual meeting, Miami, October 2010:

Optimization of Beam Orientations for SBRT Treatment Planning Using PARETO

Methods:

Multi-objective fluence and beam orientation optimization was achieved through a powerful evolutionary algorithm within PARETO. This genetic algorithm intelligently varied all beam orientations to simultaneously optimize all objective functions (based on mean dose for the OARs and PTV). Additionally, fluence gradients were optimized to spare OARs and produce a uniform dose distribution within the PTV. Over many iterations, the entire family of Pareto-optimal treatment plans, spanning a multi-dimensional trade-off surface, was mapped out. Pareto-optimal solutions were stored in a database and trade-offs between the competing objectives were visualized graphically and explored.

Results and Conclusions:

The efficacy of the solutions provided by PARETO was evaluated using the BrainLAB iPlan TPS [BrainLAB Inc., Westchester, Ill.] with five coplanar intensity-modulated treatment beams for a paraspinal phantom consisting of three OARs (cord, left and right kidneys) surrounding a horseshoe-shaped PTV. It was observed that the best and worst plans for each OAR, as selected from the Pareto surface, defined the limits of a spectrum of possible dose-volume histograms for that structure. This work demonstrated that the objective functions within PARETO had a strong correlation to the dose distribution. Thus, from many Pareto-optimal plans, the clinician may select the plan, which they decide is the most appropriate multi-objective compromise for a patient.

13. Modifications and Extensions of PARETO

Since various modifications can be made in the invention as herein above described, and many apparently widely different embodiments of same made within the spirit and

The invention claimed is:

1. A radiation therapy optimization method for a multi-objective optimization problem comprising a planning-target-volume surrounded by organs-at-risk in a patient to be treated using radiation, the method comprising:
representing computed tomography data of the patient as a three-dimensional grid of coordinates divided into voxels which contain the planning-target-volume and the organs-at-risk;
using a multi-objective optimizer to search successive generations of trial solutions to generate a database of optimized solutions that form a Pareto non-dominated set of solutions, which sample an estimation of a Pareto front to the multi-objective optimization problem where all solutions on the Pareto front are regarded as equally optimal, each trial solution being specified by a set of parameters defining beam orientations and fluence patterns which together define the radiation;
evaluating each generation of trial solutions by:
estimating a radiation dose proxy to each voxel for each trial solution to the multi-objective optimization problem;
associating a fitness function with each of the organs-at risk and the planning-target-volume;
calculating a set of fitness values for each trial solution by evaluating the fitness functions associated with the trial solution using the respective radiation dose proxies of the respective voxels associated with the trial solution such that the fitness values are optimized with respect to Pareto-optimality of the trial solutions; and
determining the Pareto non-dominated set of solutions to be optimized solutions by comparing the fitness values of the trial solutions to one another and to the fitness values of the optimized solutions of previous generations of the trial solutions;
continuing to generate successive generations of the trial solutions according to a defined convergence criterion until the optimized solutions are determined according to prescribed criteria to be approximate Pareto-optimal solutions to the multi-objective optimization problem; and
displaying the Pareto non-dominated set of solutions to a user by means of an interactive graphical interface;
wherein the set of parameters defining the radiation of each trial solution includes beam orientations and fluence patterns for each one of a number of beams of radiation; and
wherein the number of beams of radiation is optimized by:
first beams closer than a certain minimum angle being merged together to form a single beam at an intermediate angle defined by fluence parameters constructed by averaging together parameters of the first beams;
a penalty function being defined to prefer solutions requiring a fewer number of beams;
beams being sorted by gantry angle, thus rearranging an order of their defining parameters, and being re-inserted into a genetic algorithm population;
a size of a space of the parameters being reduced by sorting beams by gantry angle; and
beam averaging being applied recursively.

2. The method according to claim 1 including fluence for each beam over a variable PTV margin size being defined by a parameter that is optimized during a run according to the fitness functions such that the fluence is zero external to the variable PTV margin size.

3. The method according to claim 1 including rejecting beam orientations that cannot be realized by treatment hardware by setting all fitness values to a large number that increases with a degree to which hardware constraints are violated.

4. The method according to claim 1 including estimating the radiation dose proxy to each voxel by using rays in a ray-tracing algorithm to determine which voxels are intersected by each beam and estimating an exponential function to calculated radiation intensities by using a compact approximation of the exponential function.

5. The method according to claim 1 including:
specifying an organ type for each organ-at-risk and associating a fitness function with each organ-at-risk based on the organ type specified; and
defining a simple volumetric fitness function for volumetric organs-at-risk by the following equation:

$$F_{OAR,VOL} = \frac{N_{OAR,i}^{-1} \sum_{i=1}^{N} D_{OAR,i}}{M^{-1} \sum_{i=1}^{M} D_{PTV,i}}$$

representing the mean organ-at-risk dose, normalized to mean PTV dose, where $D_{OAR,i}$ and $D_{PTV,i}$ are OAR and PTV dose respectively; and N and M are the number of OAR and PTV voxels respectively.

6. The method according to claim 1 including:
specifying an organ type for each organ-at-risk and associating a fitness function with each organ-at-risk based on the specified organ type; and
defining a simple serial fitness function for serial organs-at-risk by the following equation:

$$F_{OAR,SER} = \frac{\max(D_{OAR})}{M^{-1} \sum_{i=1}^{M} D_{PTV,i}}$$

representing the maximum organ-at-risk dose, normalized to mean PTV dose, where $\max(D_{OAR})$ is OAR dose maximized over all OAR voxels; $D_{PTV,i}$ is PTV dose applied to voxel i; and M is the number of PTV voxels.

7. The method according to claim 4 including defining a DVH fitness function for volumetric or serial organs-at-risk by the following equation:

$$F_{OAR} = \frac{1}{V_{OAR}} \left[ \sum_{i=1}^{N} f_i^p \Delta V_{OAR,i} \right]^{1/p} ; f_i \equiv \left\{ \begin{array}{ll} 0, & D_i \leq D_0 \\ D_i/D_0, & D_i > D_0 \end{array} \right\}$$

representing the volume-weighted mean thresholded dose computed from a dose-volume histogram (DVH) with N bins, where $\Delta V_{OAR,i}$ is the increment in volume from the i'th bin of the DVH and $V_{OAR}$ is the total volume; $D_i$ is dose associated with DVH bin i; and $D_0$ is the target dose threshold for the OAR; such that voxels receiving the highest dose are more strongly suppressed for larger values of exponent p≥1; where a value of p=1 is appropriate for volumetric structures, while p>1 is appropriate for serial structures.

8. The method according to claim 1 further comprising:
defining a hot zone as a set of voxels near the PTV such that $d_i <= f_{PTV} * d_{PTV}$ where $d_i$ is the distance from voxel i to the nearest voxel within the PTV; $f_{PTV}$ is a fractional value less than or equal to 0.5; and $d_{PTV}$ is the maximum distance between voxels within the PTV;
defining a cool zone as a set of voxels outside the hot zone and within the patient skin;
defining a penalty function to suppress radiation hotspots by the equation:

$$F_{penalty} {}^* = F_0 {}^* (1 + \max\{d_i/d_0 | d_i > f_{PTV} {}^* d_{PTV} \text{ and } D_i > D_{OHT}; i \in \{1 \ldots N\}\})$$

where $d_i$ is the distance from voxel i within the treatment volume to the nearest voxel within the PTV structure; do is the maximum value of $d_i$ over all voxels in the treatment volume; $f_{PTV}$ is a fractional value less than or equal to 0.5; $d_{PTV}$ is the maximum distance between voxels within the PTV, such that the product $f_{PTV} {}^* d_{PTV}$ defines the size of the allowed hot zone near the PTV; $D_i$ is the dose received by voxel i; $D_{OHT}$ is the maximum desired dose to other healthy tissue outside the hot zone; and N is the number of voxels within the treatment volume; and wherein distance $d_i$ can be calculated exactly, or rapidly estimated according to the following procedure:
defining n to be an integer greater than approximately 25;
defining a matrix R of radii such that $R = [(X-x_0)^2 + (Y-y_0)^2 + (Z-y_0)^2]^{1/2}$ where X, Y, and Z are matrices of Cartesian coordinate values for the voxels constructed from coordinate vectors x, y, and z; and $x_0$, $y_0$, and $z_0$ are the coordinates of a central voxel such that $x_0 = x(\text{floor}((Nx/2)+1))$, $y_0 = x(\text{floor}((Ny/2)+1))$, and $z_0 = z(\text{floor}((Nz/2)+1))$ where Nx, Ny, and Ny are the lengths of coordinate vectors x, y, and z respectively;
redefining values of R equal to zero to be equal to the smallest non-zero value of R; and
calculating a matrix of distances $d = \{d_i\}$ by performing the convolution: $d = [\text{conv}(M, R^{-n})]^{1/n}$.

9. The method according to claim 1 wherein the set of parameters defining the radiation of each trial solution includes dose rate, parameters defining an orientation of non-coplanar arcs, beam directions, and aperture shape for volumetric modulated arc therapy.

10. The method according to claim 1 including using a clustering algorithm to discover distinct families of solutions in a space of the parameters.

11. The method according to claim 1 including ghosting of previously viewed solutions, for rapid and intuitive comparison with previously viewed solutions.

12. The method according to claim 1 wherein the prescribed criteria for determining the optimized solutions to be a set of converged Pareto non-dominated solutions comprises no fitness values being improved by a prescribed amount in a prescribed number of previous generations of trial solutions.

13. A radiation therapy optimization method for a multi-objective optimization problem comprising a planning-target-volume surrounded by organs-at-risk in a patient to be treated using radiation, the method comprising:

representing computed tomography data of the patient as a three-dimensional grid of coordinates divided into voxels which contain the planning-target-volume and the organs-at-risk;
using a multi-objective optimizer to search successive generations of trial solutions to generate a database of optimized solutions that form a Pareto non-dominated set of solutions, which sample an estimation of a Pareto front to the multi-objective optimization problem where all solutions on the Pareto front are regarded as equally optimal, each trial solution being specified by a set of parameters defining beam orientations and fluence patterns which together define the radiation;
evaluating each generation of trial solutions by:
estimating a radiation dose proxy to each voxel for each trial solution to the multi-objective optimization problem;
associating a fitness function with each of the organs-at risk and the planning-target-volume;
calculating a set of fitness values for each trial solution by evaluating the fitness functions associated with the trial solution using the respective radiation dose proxies of the respective voxels associated with the trial solution such that the fitness values are optimized with respect to Pareto-optimality of the trial solutions; and
determining the Pareto non-dominated set of solutions to be optimized solutions by comparing the fitness values of the trial solutions to one another and to the fitness values of the optimized solutions of previous generations of the trial solutions;
continuing to generate successive generations of the trial solutions according to a defined convergence criterion until the optimized solutions are determined according to prescribed criteria to be approximate Pareto-optimal solutions to the multi-objective optimization problem;
displaying the Pareto non-dominated set of solutions to a user by means of an interactive graphical interface; and
defining a conformity fitness function of the planning-target-volume by the following equation:

$$F_{PTV} = \log_{10}\left\{\frac{1}{2}\left[1 - \frac{\sum_{i=1}^{N} Q_i(D_i - \overline{D})(M_i - \overline{M})}{\sigma_D \sigma_M}\right]\right\}$$

$$\sigma_D = \left(\frac{\sum_{i=1}^{N} Q_i(D_i - \overline{D})^2}{\sum_{i=1}^{N} Q_i}\right)^{\frac{1}{2}} \quad \sigma_M = \left(\frac{\sum_{i=1}^{N} Q_i(M_i - \overline{M})^2}{\sum_{i=1}^{N} Q_i}\right)^{\frac{1}{2}}$$

wherein the conformity fitness function is based on a statistical correlation function between a dose proxy matrix D and a planning-target-volume mask M, where M is defined such that a value of 1 is assigned to all voxels inside the PTV and 0 outside; $\sigma_D$ and $\sigma_M$ are the weighted dose and mask standard deviations, respectively; N is the total number of voxels inside the patient volume; and weight matrix Q determines the relative weight applied interior and exterior to the PTV.

14. A radiation therapy optimization method for a multi-objective optimization problem comprising a planning-target-volume surrounded by organs-at-risk in a patient to be treated using radiation, the method comprising:

representing computed tomography data of the patient as a three-dimensional grid of coordinates divided into voxels which contain the planning-target-volume and the organs-at-risk;

using a multi-objective optimizer to search successive generations of trial solutions to generate a database of optimized solutions that form a Pareto non-dominated set of solutions, which sample an estimation of a Pareto front to the multi-objective optimization problem where all solutions on the Pareto front are regarded as equally optimal, each trial solution being specified by a set of parameters defining beam orientations and fluence patterns which together define the radiation;

evaluating each generation of trial solutions by:
    estimating a radiation dose proxy to each voxel for each trial solution to the multi-objective optimization problem;
    associating a fitness function with each of the organs-at risk and the planning-target-volume;
    calculating a set of fitness values for each trial solution by evaluating the fitness functions associated with the trial solution using the respective radiation dose proxies of the respective voxels associated with the trial, solution such that the fitness values are optimized with respect to Pareto-optimality of the trial solutions; and
    determining the Pareto non-dominated set of solutions to be optimized solutions by comparing the fitness values of the trial solutions to one another and to the fitness values of the optimized solutions of previous generations of the trial solutions;

continuing to generate successive generations of the trial solutions according to a defined convergence criterion until the optimized solutions are determined according to prescribed criteria to be approximate Pareto-optimal solutions to the multi-objective optimization problem; and displaying the Pareto non-dominated set of solutions to a user by means of an interactive graphical interface;

wherein the set of parameters defining the radiation of each trial solution includes dose rate, non-coplanar arcs, beam directions, and aperture shape for stereotactic radiosurgery.

15. A radiation therapy optimization method for a multi-objective optimization problem comprising a planning-target-volume surrounded by organs-at-risk in a patient to be treated using radiation, the method comprising:

representing computed tomography data of the patient as a three-dimensional grid of coordinates divided into voxels which contain the planning-target-volume and the organs-at-risk;

using a multi-objective optimizer to search successive generations of trial solutions to generate a database of optimized solutions that form a Pareto non-dominated set of solutions, which sample an estimation of a Pareto front to the multi-objective optimization problem where all solutions on the Pareto front are regarded as equally optimal, each trial solution being specified by a set of parameters defining beam orientations and fluence patterns which together define the radiation;

evaluating each generation of trial solutions by:
    estimating a radiation dose proxy to each voxel for each trial solution to the multi-objective optimization problem;
    associating a fitness function with each of the organs-at risk and the planning-target-volume;
    calculating a set of fitness values for each trial solution by evaluating the fitness functions associated with the trial solution using the respective radiation dose proxies of the respective voxels associated with the trial solution such that the fitness values are optimized with respect to Pareto-optimality of the trial solutions; and
    determining the Pareto non-dominated set of solutions to be optimized solutions by comparing the fitness values of the trial solutions to one another and to the fitness values of the optimized solutions of previous generations of the trial solutions;

continuing to generate successive generations of the trial solutions according to a defined convergence criterion until the optimized solutions are determined according to prescribed criteria to be approximate Pareto-optimal solutions to the multi-objective optimization problem; and displaying the Pareto non-dominated set of solutions to a user by means of an interactive graphical interface;

wherein the set of parameters defining the radiation of each trial solution includes beam orientations and fluence patterns for each one of a number of beams of radiation; and wherein all parameters defining the radiation and the fitness functions together comprise a single monolithic optimization problem in which all parameters are treated identically and varied simultaneously by the optimizer to optimize the fitness functions.

\* \* \* \* \*